(12) United States Patent
Yanuma

(10) Patent No.: US 12,727,938 B2
(45) Date of Patent: Sep. 8, 2026

(54) TREATMENT TOOL AND MANIPULATING METHOD FOR TREATMENT TOOL

(71) Applicant: OLYMPUS MEDICAL SYSTEMS CORP., Tokyo (JP)

(72) Inventor: Yutaka Yanuma, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 600 days.

(21) Appl. No.: 18/110,479

(22) Filed: Feb. 16, 2023

(65) Prior Publication Data

US 2023/0263569 A1 Aug. 24, 2023

Related U.S. Application Data

(60) Provisional application No. 63/313,659, filed on Feb. 24, 2022.

(51) Int. Cl.
*A61B 18/14* (2006.01)
*A61B 18/00* (2006.01)

(52) U.S. Cl.
CPC *A61B 18/1492* (2013.01); *A61B 2018/00202* (2013.01); *A61B 2018/00601* (2013.01)

(58) Field of Classification Search
CPC ...... A61B 18/1492; A61B 2018/00202; A61B 2018/00601
See application file for complete search history.

(56) References Cited

U.S. PATENT DOCUMENTS 7,635,363 B2 12/2009 Hutchins et al.
12,005,200 B2 * 6/2024 Maekubo .......... A61M 25/0136
2021/0046285 A1 2/2021 Maekubo et al.
2021/0196926 A1 * 7/2021 Malinaric .............. A61B 5/068
2021/0236105 A1 * 8/2021 Hansen ............ A61B 17/00234
2022/0401147 A1 * 12/2022 Tang .................. A61B 18/1815

FOREIGN PATENT DOCUMENTS

CN 112449585 A 3/2021
JP 2021-183071 A 12/2021
WO WO-2021016699 A1 * 2/2021 ......... A61B 17/1671

OTHER PUBLICATIONS

Office Action dated Sep. 26, 2025, issued in corresponding Chinese Patent Application No. 202310051558.1.
Office Action dated Apr. 23, 2026, issued in corresponding Chinese Patent Application No. 202310051558.1.

* cited by examiner

*Primary Examiner* — Linda C Dvorak
*Assistant Examiner* — Abigail Bock
(74) *Attorney, Agent, or Firm* — Morgan, Lewis & Bockius LLP

(57) ABSTRACT

The treatment tool including: a tube including a lumen extending in a longitudinal axis of the tube; a wire inserted into the lumen and extending along the longitudinal axis of the tube; a first handle connected to a proximal end portion of the wire; a second handle attached to a proximal end portion of the tube. In a first configuration, the first handle is rotatable relative to the second handle about a rotation axis. In a second configuration, the first handle is non-rotatable relative to the second handle when an applied force applied to the first handle in a rotation direction is equal to or less than a predetermined amount. The first handle is rotatable relative to the second handle when the applied force is greater than the predetermined amount.

9 Claims, 16 Drawing Sheets

TREATMENT TOOL AND MANIPULATING METHOD FOR TREATMENT TOOL

RELATED APPLICATION DATA

This application is based on and claims priority under 35 U.S.C. § 119 to U.S. Application No. 63/313,659 filed on Feb. 24, 2022, the entire contents of which are incorporated herein by reference.

FIELD OF THE DISCLOSURE

The present disclosure relates to a treatment tool and a manipulating method for the treatment tool.

BACKGROUND

When a bile duct calculi is removed by an endoscope, there is a case that some calculi cannot be removed in their original size due to their size larger than a duodenal papilla which is an outlet of a bile duct. In this case, the endoscope treatment tools performing an incision treatment of a tissue, a papillotome or the like, for example, disclosed in U.S. Pat. No. 7,635,363 specification has been used. Namely, an endoscope treatment tool such as a papillotome or the like is inserted through an endoscope, a duodenal papilla and sphincter muscles are incised to widening an outlet of the bile duct, after that, the calculi are retrieved. A position of an encircling fold is approximately coincident with a direction in which the bile duct extends around the duodenal papilla. Since blood vessels are sparse and bleeding hardly occurs in the direction in which the bile duct extends around the duodenal papilla, sphincter muscles are generally incised in the direction of the encircling fold.

In such a papillotome using incision of sphincter muscles, when a knife portion, which is arranged at a pre-curved portion on a distal end part of a sheath main body and protrudes from an outer circumferential surface of the sheath, is protruded from a distal end of an endoscope for a pancreas, an orientation of the knife portion may be automatically oriented at approximately the 12 o'clock direction in an endoscopic image.

An insertion portion of an endoscope is inserted from a mouth of a patient to the duodenal papilla, and a papillotome is then inserted into a channel of the insertion portion, whereby the papillotome is made to protrude from a distal end of the insertion portion of the endoscope. In the course of the insertion, an insertion portion of the papillotome is passively bent at multiple positions along a path from a manipulation portion to a treatment portion. In a conventional papillotome having a rotating function about an axis of a treatment portion, a knife portion may be oriented in a direction different from the 12 o'clock direction as a result of passive bending at multiple positions as mentioned hereinbefore because of the involvement of a rotational torque based on which a rotational manipulation at the manipulation portion can be transmitted to a distal end of the knife portion. If this becomes the case, it is necessary to bring the direction of the knife portion into alignment with an intended direction. Especially, a complicated manipulation will be needed to bring the direction of the pre-curved portion into alignment with a desired direction while treatment.

BRIEF SUMMARY OF EMBODIMENTS

A treatment tool according to one embodiment, includes: a tube including a lumen extending in a longitudinal axis of the tube; a wire inserted into the lumen and extending along the longitudinal axis of the tube; a first handle connected to a proximal end portion of the wire; a second handle attached to a proximal end portion of the tube. In a first configuration, the first handle is rotatable relative to the second handle about a rotation axis. In a second configuration, the first handle is non-rotatable relative to the second handle when an applied force applied to the first handle in a rotation direction is equal to or less than a predetermined amount. The first handle is rotatable relative to the second handle when the applied force is greater than the predetermined amount.

A treatment tool according to one embodiment, includes: a tube including a lumen extending in a longitudinal axis of the tube; a wire inserted into the lumen and extending along the longitudinal axis of the tube; a first handle connected to a proximal end portion of the wire; a second handle attached to a proximal end portion of the tube. The first handle advances and retracts relative to the second handle. The first handle is movable between a first position and a second position. In the first position, the second handle is engaged with the first handle in a rotation direction of the first handle. In the second position, the second handle is disengaged from the first handle in the rotation direction of the first handle.

An operation method of a treatment tool according to one embodiment, includes: advancing a treatment tool to a treatment target area in a body, the treatment tool comprising a wire inserted into a lumen of an elongated tube; rotating a first handle of the treatment tool relative to a second handle of the treatment to rotate the wire about the longitudinal axis of the elongated tube; advancing the first handle relative to the second handle to engage the first handle with the second handle. During rotating, the treatment tool generates a first user feedback from the first handle. After advancing the first handle relative to the second handle, further rotating the first handle relative to the second handle to further rotate the wire about the longitudinal axis of the elongated tube. During further rotating, the treatment tool generates a second user feedback from the first handle.

BRIEF DESCRIPTION OF THE DRAWINGS

FIG. 20 is a cross-sectional view of the handle of the second embodiment in a longitudinal direction.

DETAILED DESCRIPTION

First Embodiment

[Treatment System 100]

Figure 1:
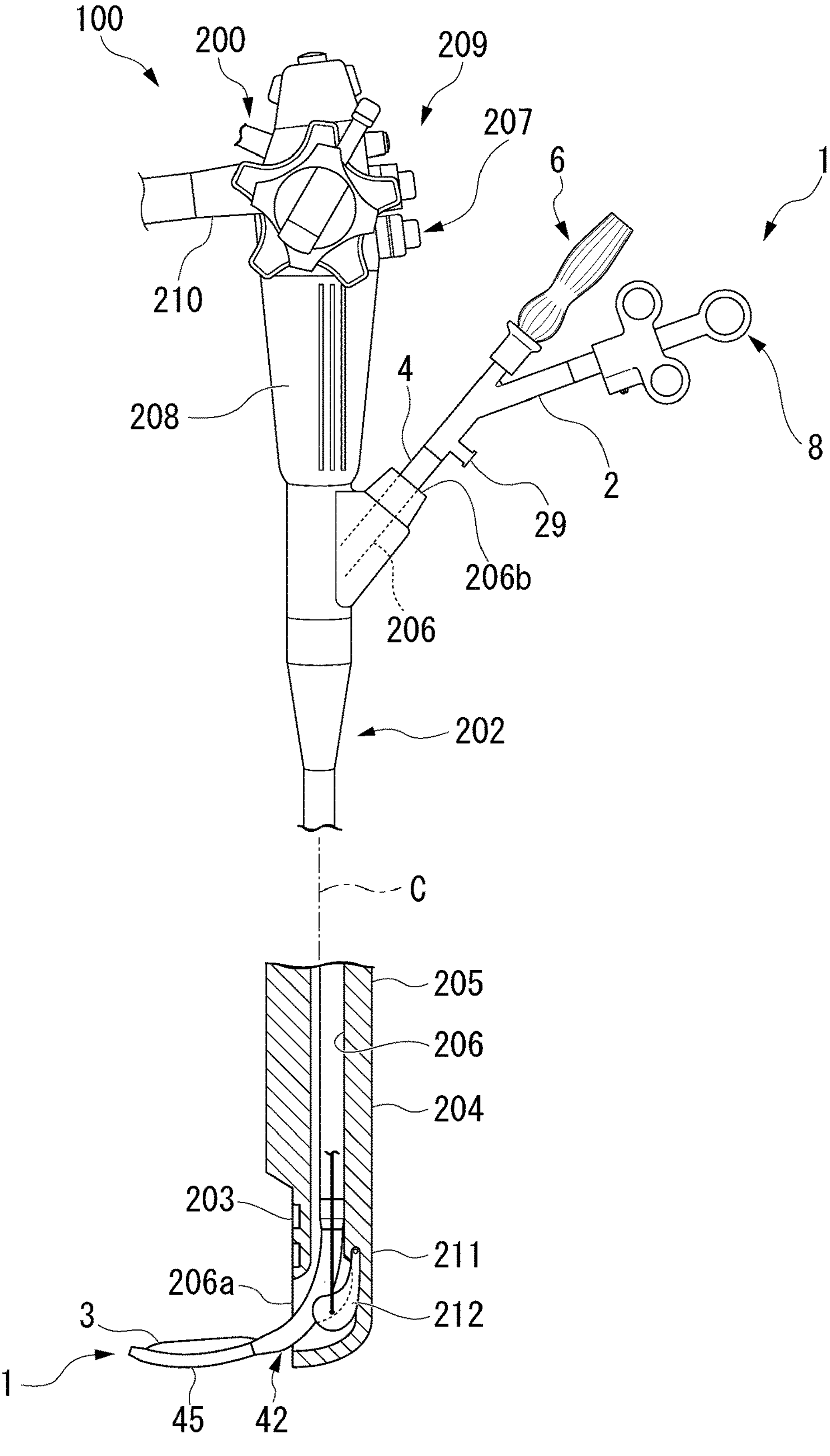
FIG. 1 is a view of an endoscope treatment system according to the first embodiment.

A treatment system 100 according to the first embodiment will be described with reference to FIG. 1. FIG. 1 is a view of the treatment system 100 provided with the treatment tool 1 according to the embodiment. As shown in FIG. 1, the treatment system 100 includes a flexible endoscope 200 and the treatment tool 1. The treatment tool 1 is used by being inserted into the flexible endoscope 200.

[Flexible Endoscope 200]

As shown in FIG. 1, the flexible Endoscope 200 (hereinafter referred to as "endoscope 200") includes an insertion portion 202 and an endoscope operation part 207. The insertion portion 202 is inserted into the body. The endoscope operation portion 207 is attached to the insertion portion. In the following description, an insertion end side inserting the insertion portion 202 into the body is referred to as a distal end side, and the endoscope operation portion 207 side is referred to as a proximal end side.

The insertion portion 202 has an imaging portion 203, an active bending portion 204, a flexible portion 205, and a distal end hard portion 211. The imaging portion 203, the active bending portion 204, the flexible portion 205, and the distal end hard portion 211 are disposed in this order from the distal end of the insertion portion 202. A channel 206 for inserting the treatment tool 1 is provided inside the insertion portion 202. A distal end opening **206*a* of the channel 206 is formed in the distal end of the insertion portion 202**.

An elevator 212 is provided inside the channel 206 vicinity of the distal opening **206*a* of the distal end hard portion 211. The elevator 212 raises the treatment tool 1 being inserted into the channel 206. An operation wire 213 is connected to a distal end portion of the elevator 212, and a proximal end of the operation wire 213 is connected to the endoscope operation portion 207 through the insertion portion 202. The operation wire 213 is only shown in FIG. 1**.

The imaging portion 203 includes, for example, CCD or CMOS, and is configured to image a treatment target part. The imaging portion 203 is configured to image an incision portion 3 of the treatment tool 1 which is to be described later, in a state where the treatment tool 1 protrudes from the distal end opening **206*a* of the channel 206. The active bending portion 204 can be positively bent in response to an operation of the endoscope operation portion 207 by an operator. The flexible portion 205** is a tubular part having flexibility.

The endoscope operation portion 207 is connected to the flexible portion 205. The endoscope operation portion 207 has a grip 208, an input portion 209, a forceps port **206*b*, and a universal cord 210. The grip 208 is a part grasped by the operator. The input portion 209 receives an operation input for bending the active bending portion 204. The forceps port 206*b* is an opening communicating with the channel 206 and for inserting into or pulling out the treatment tool relative to the channel 206. The universal code 210 outputs an image captured by the imaging portion 203 to the outside. The universal cord 210** is configured to be connected to a display device such as a liquid crystal device via an image processing device such as a processor.

[Treatment Tool 1]

Figure 2:
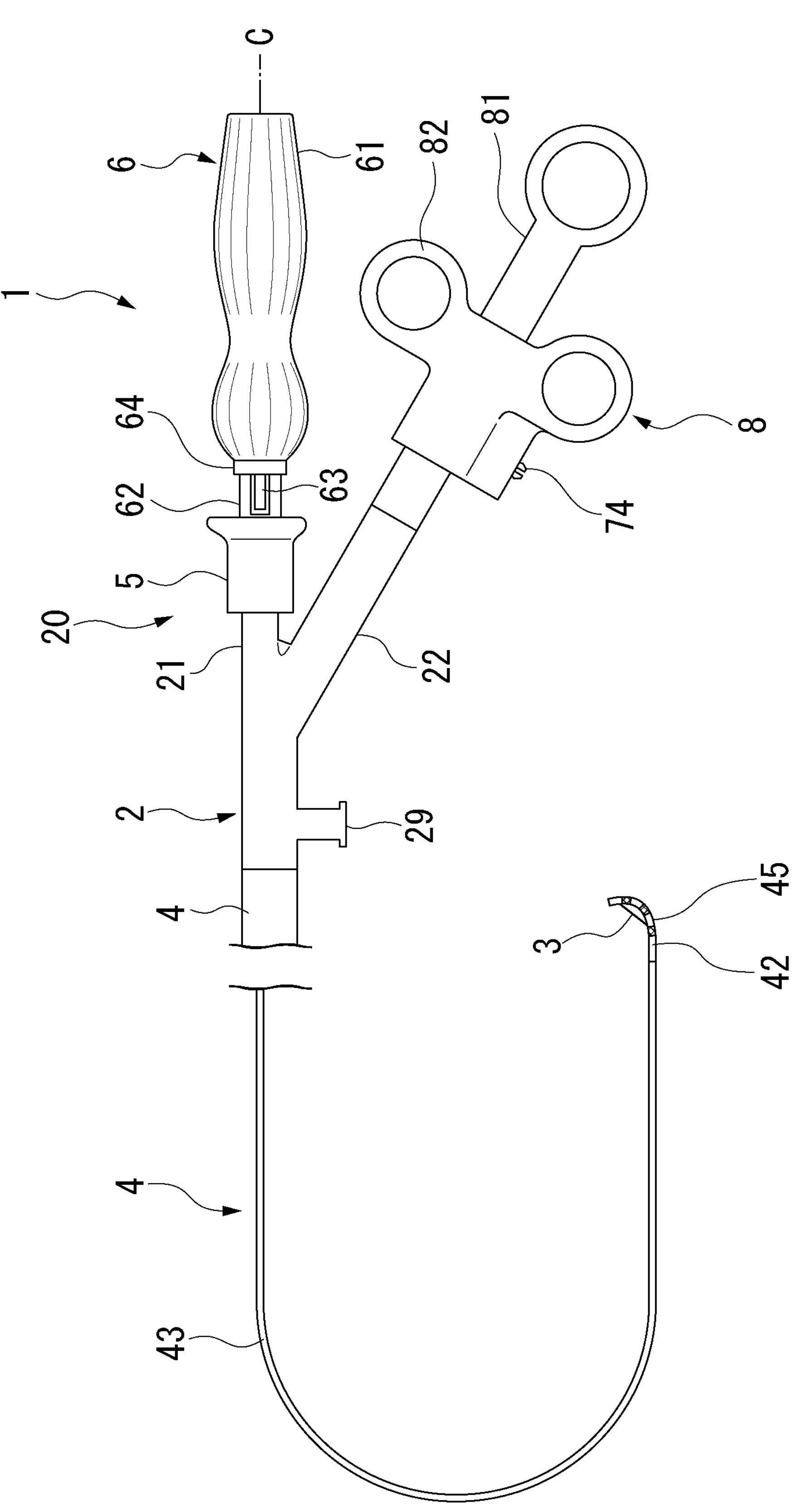
FIG. 2 is a view of a treatment instrument according to the first embodiment.
Figure 3:
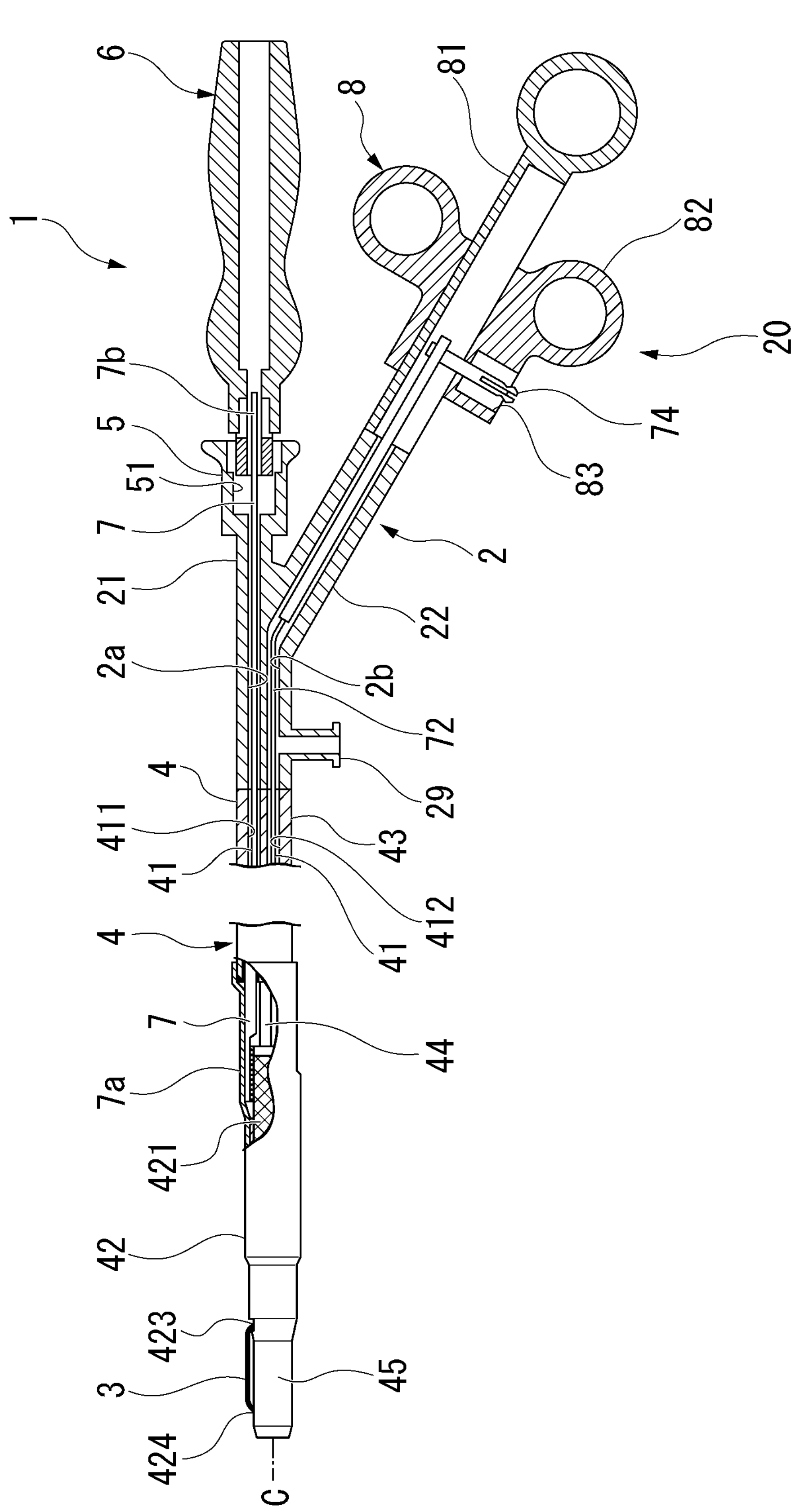
FIG. 3 is a partial cross-sectional view of the treatment tool according to the first embodiment in a longitudinal direction.
Figure 4:
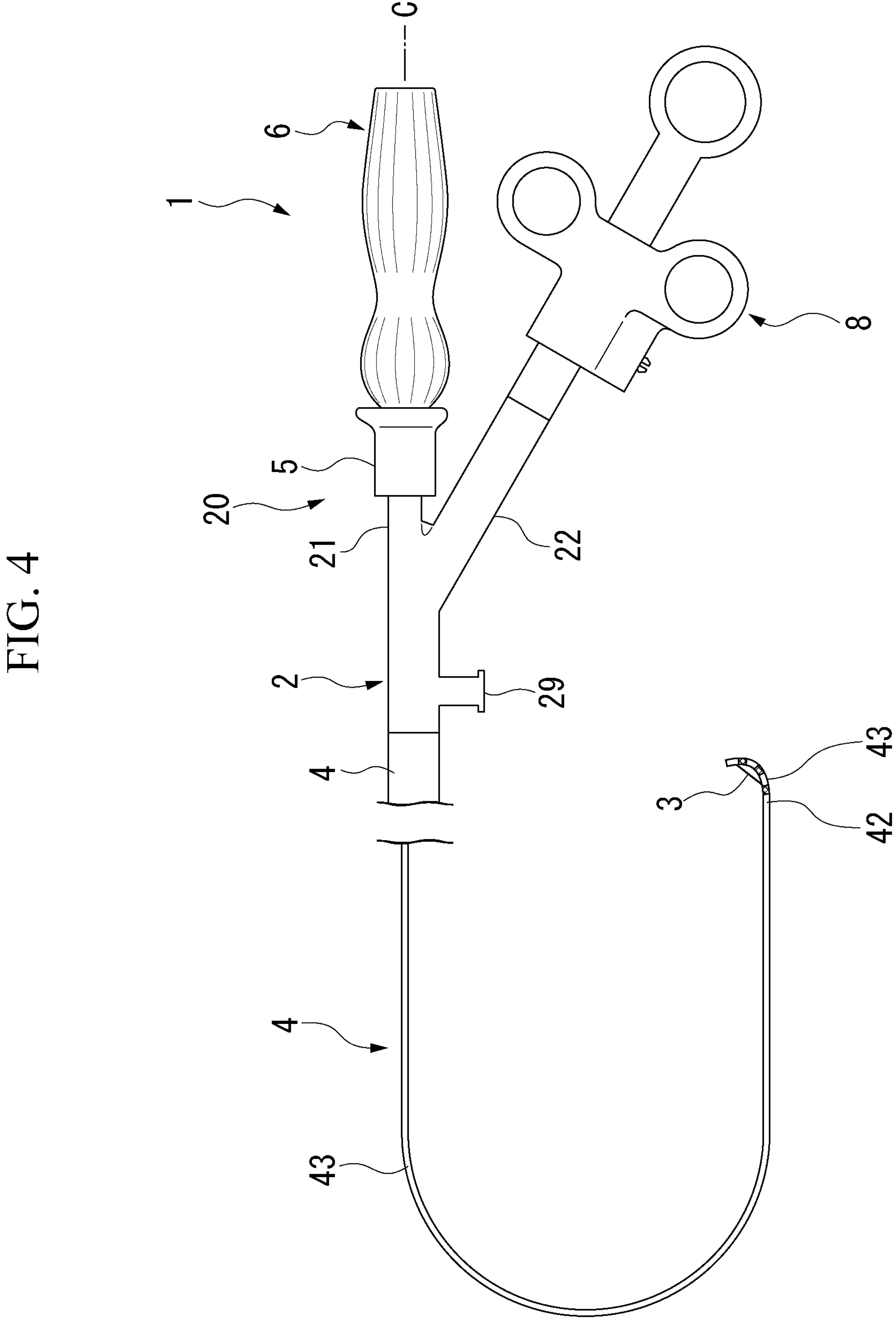
FIG. 4 is a view of the treatment instrument according to the first embodiment.

FIG. 2 to FIG. 4 are overall views showing the treatment tool 1. FIG. 3 shows a treatment tool 1 partially shows in a cross-sectional view. The treatment tool 1 is used by being inserted into the endoscope 200. As shown in FIG. 2 to FIG. 4, the treatment tool 1 has a sheath 4 (tube), an operation portion 20, and a torque wire 7 (wire, see FIG. 3), and the incision portion 3.

The sheath 4 is an elongated member having a lumen 41 extended along a longitudinal direction thereof. The sheath 4 has an outer diameter being insertable into the channel 206. The sheath 4 is a flexible sheath made of resin. The sheath 4 is a multi-lumen tube having a plurality of lumen. The plurality of lumen 41 includes a wire insertion lumen for the torque wire 7 and a conductive wire 72 or the like, and a liquid supply lumen. FIG. 3 only shows a first lumen 411 (lumen) for inserting the torque wire 7 and a second lumen 412 for inserting the conductive wire 72.

The sheath 4 has a distal sheath 42, a proximal sheath 43, and a plurality of connection tube 44. The distal sheath 42 and the proximal sheath 43 are arranged in line apart from each other in the longitudinal axis direction. The plurality of connection tube 44 are provided between the distal sheath 42 and the proximal sheath 43. The connection tubes 44 are a tube connecting each lumen of the distal sheath 42 and each lumen of the proximal sheath 43.

As shown in FIG. 3, a blade 421 is provided on a proximal end portion of the distal sheath 42. The blade 421 is fixed to the distal sheath 42 by an adhesion or a thermal shrink tube or the like. A member, for example, a tubular member in which a plurality of narrow wires is bundled and is used as a blade. A member, for example: a member having a tubular shape by bundling a plurality of thin wire and weaving in a lattice shape; a member having a tubular shape by winding a stainless steel wire or a stainless steel band to be in a single strand or multiple strand coil shape; and a member having a tubular shape in which a single strand or multiple strand coil is wounded in alternatively reverse direction to be in a multi-layer, used as the blade 421.

The distal sheath 42 may include a pre-curved portion 45. The pre-curve portion 45 has a restoring force into a bent shape that the distal sheath 42 is bent in a predetermined direction. As shown in FIG. 4, the pre-curve portion 45 is bent so that an outer circumferential surface, in which through-holes 423 and 424 for drawing the incision portion 3 toward an outside of the distal sheath 42 are formed, is located on an inner side of the bent.

A central axis C of the torque wire 7 elongates along a longitudinal axis of the sheath 4 and the torque wire 7 is inserted into a first lumen 411 of the proximal sheath 43. The torque wire 7 transmits a rotation torque being input to the operation portion 20 to the distal sheath 42, and makes the distal sheath 42 to rotate about the central axis C. A distal end of the torque wire 7 elongates to more distal side than a distal end of the proximal sheath 43 and the distal end of the torque wire 7 is fixed to a proximal end of the blade 421. A distal end portion of the torque wire 7 includes a planar portion, and the planar portion is attached and fixed to the blade 421 (see FIG. 3). A proximal end portion 7*b* of the torque wire 7 includes a planner portion, and the planner portion is inserted into and fixed to the rotation handle 6 (first handle, see FIG. 7). The torque wire 7 is, for example, the single-strand wire. The torque wire 7 may be a wire formed by bundling a plurality of element wires, or the like. The torque wire 7 can be formed, for example, with stainless steel or a nickel-titanium alloy.

The torque wire 7 is inserted into the first lumen 411 such that the torque wire 7 is rotatable about the central axis C relative to the first lumen 411 by a rotating manipulation of the rotation handle 6 about the central axis C (rotation axis). On the other hand, since the distal end of the torque wire 7 is fixed to the distal sheath 42, when the rotation handle 6 is rotationally manipulated about the central axis C, a rotational torque is transmitted via the torque wire 7 and the distal sheath 42 can be rotated relative to the proximal sheath 43 about the longitudinal axis.

The incision portion 3 protrudes from an outer circumferential surface of the distal sheath 42, and provided so as to be elongated along the longitudinal axis of the sheath 4. The incision portion 3 is constituted by a part of the conductive wire 72. Specifically, the conductive wire 72 is formed of a core wire having conductivity and an unillustrated insulating coating formed from an appropriate synthetic resin. The conductive wire 72 extends from the second lumen 412 to an outside of the sheath 4 at the through-hole 423 of the distal sheath 42, is disposed extending along the longitudinal axis of the sheath 4 toward the distal side, and enters the second lumen 412 from the through-hole 424 on the distal side thereof. A distal end of the conductive wire 72 is fixed to an inside of the second lumen 412. A portion of the conductive wire 72, the portion being exposed from the through-holes 423, 424 to the outside of the sheath 4, is not covered with the insulating coating, so that the core wire is exposed to configure the incision portion 3 that can incise a tissue. The incision portion 3 is an example of the electrode.

The operation portion 20 is attached to a proximal end portion of the sheath 4. The operation portion 20 includes a handle main body 2 (second handle), a rotation handle 6 (first handle), and a knife handle 8. The handle main body 2 is connected to a proximal end of the sheath 4. The rotation handle 6 and the knife handle 8 are provided so as to be advanceable and retractable relative to the handle main body 2.

The handle main body 2 includes a connection portion 21 of the rotation handle 6 and a connection portion 22 of the knife handle 8 which are branched at a proximal end part of the handle main body 2. As shown in FIG. 3, the connection portion 21 of the rotation handle 6 is disposed coaxial with the longitudinal direction of the sheath 4. A torque wire lumen 2*a* elongating coaxial with the central axis C of the first lumen 411 of the sheath 4 is formed in the handle main body 2. The connection portion 22 of the knife handle 8 is provided to elongate in a direction crossing the longitudinal direction of the sheath 4. A conductive wire lumen 2*b* communicating with the second lumen 412 of the sheath 4 is formed in the handle main body 2. The conductive wire lumen 2*b* elongates coaxial with the central axis C of the sheath 4 at the distal end part of the handle main body 2 and bend and elongates in a crossing direction relative to the longitudinal axis of the second lumen 412 at the proximal end part of the handle main body 2. In consideration of the operability, the connection portion 22 of the knife handle 8 may be enough to be positioned not to interfere a manipulation of the rotation handle 6. The configuration that the connection portion 22 of the knife handle 8 is disposed to across the longitudinal direction of the sheath 4 is not limited.

A liquid supply port 29 communicating with the liquid supply lumen is provided on the handle main body 2. An unillustrated syringe can be detachably attached to the fluid supply port 29. An example shown in FIG. 3, the second lumen 412 communicates with the liquid supply port 29. The second lumen 412 also functions as a liquid supply lumen.

The knife handle 8 is a manipulation portion for advancing and retracting manipulation of the conductive wire 72 and for bending manipulation of the distal sheath 42. The knife handle 8 includes a handle shaft 81, a slider 82, and a terminal port 83. A distal end of the handle shaft 81 is a member attaching the connection portion 22 of the handle main body 2. The slider 82 is provided to be slidable relative to the handle shaft 81. The terminal port 83 is provided on the slider 82. A proximal end portion of the conductive wire 72 is inserted into the handle shaft 81 through the conductive wire lumen 2*b* of the handle main body 2, elongates to a vicinity of the terminal port 83, and is connected to a terminal 74. The terminal 74 is provided inside the terminal port 83 and fixed to the slider 82. The terminal 74 is capable of connecting to an external high-frequency power source. The external high-frequency power supplied from the external high-frequency power source is supplied to the conductive wire 72 via the terminal 74. In a case where the slider 82 advances relative to the handle shaft 81, it can be in a state that the incision portion 3 is in an approximately straight and the incision portion 3 is made to be disposed along with the outer circumferential surface of the distal sheath 42. In a case where the slider 82 retracts relative to the handle shaft 81, the distal sheath 42 is relatively bent so that the incising portion 3 can be brought into a taut state (see FIG. 2).

Figure 5:
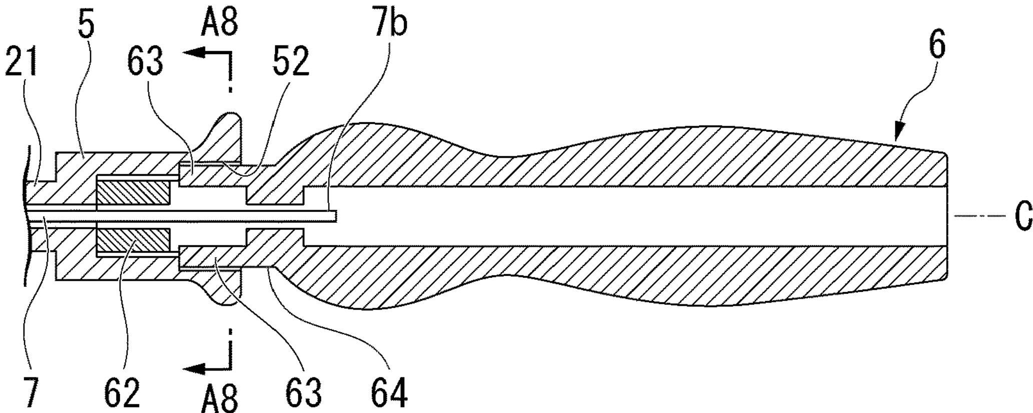
FIG. 5 is a cross-sectional view of a rotation handle of the first embodiment in a longitudinal direction.
Figure 6:
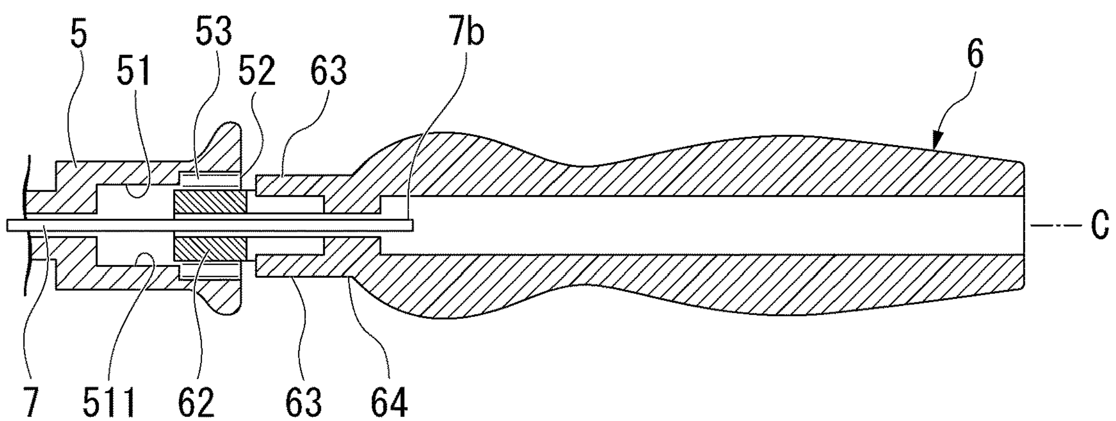
FIG. 6 is a cross-sectional view of the rotation handle of the first embodiment in a longitudinal direction.
Figure 8:
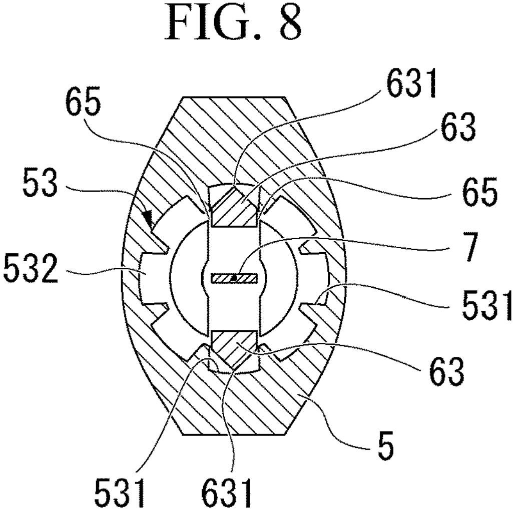
FIG. 8 is a cross-sectional view in A8-A8 line shown in FIG. 5.

The handle main body 2 includes a socket 5. The socket 5 is provided at the connection portion 21 of the rotation handle 6. The socket 5 is configured to fitting with the rotation handle 6. FIG. 5 and FIG. 6 are cross-sectional views of a portion of the socket 5 and the rotation handle 6 in the longitudinal direction. FIG. 5 shows a state that the rotation handle 6 is fitted into the socket 5. FIG. 6 shows a state that the rotation handle 6 is drawn out from the socket 5. FIG. 8 is a cross-sectional view in arrows A8-A8 line shown in FIG. 5. As shown in FIG. 5 and FIG. 6, an insertion port 51 communicating with a proximal opening of the torque wire lumen 2*a* is formed in the socket 5. The insertion port 51 is an approximately cylindrical shape opening having a size into which an insertion portion of the rotation handle 6 can be inserted.

A locking portion 53 is formed in an inner circumferential surface 511 of the socket 5. As shown in FIG. 8, the locking portion 53 includes a plurality of convex portions 531 (second protrusions) and a plurality of concave portions 532 (recesses). The plurality of concave-convex portions 531 and 532 of the locking portion 53 is arranged on the insertion port 51 of the socket 5 side by side in a circumferential direction. The plurality of concave-convex portions 531 and 532 are arranged on the inner circumferential surface 511 with equal intervals in the circumferential direction. The number of the plurality of concave-convex portions 531 and 532 are not limited to an example shown in figures. The locking portion 53 elongates distally from a proximal opening 52 of the insertion port 51 to a middle portion in the longitudinal direction. The locking portion 53 is configured such that the plurality of concave portions 532 is formed on a proximal part of the inner circumferential surface 511 of the insertion port 51. Therefore, in a radial direction of the insertion port 51, protruding ends of the convex portions 531 are positioned same on the inner circumferential surface 511 of a distal end side of the insertion port 51, or on outside from inner circumferential surface 511.

In the embodiment, although an example that the socket 5 is configured to be integrally constituted with the handle main body 2 is shown, the socket 5 and the connection portion 21 of the handle main body 2 may be separately constituted. Although an example that a pair of protrusions are provided in the rotation handle 6 is shown, the number of protrusions is not limited to an example shown in figures. The protrusion may be enough to be capable of locking with the concave-convex portions of the locking portion 53, and may provide one or more convex.

Figure 7:
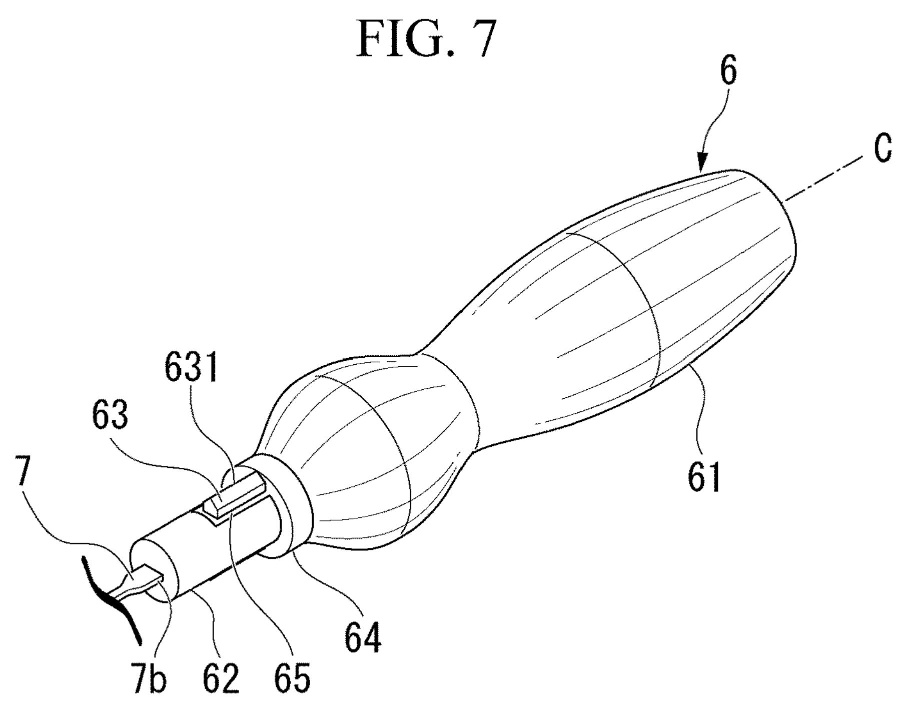
FIG. 7 is a perspective view of the rotation handle of the first embodiment.

The rotation handle 6 is connected to a proximal end portion 7*b* of the torque wire 7. The rotation handle 6 is provided to be rotatable relative to the handle main body 2 about the central axis C. FIG. 7 shows a perspective view of the rotation handle 6. The rotation handle 6 includes a grip 61, an insertion portion 62, and a protrusion 63 (first protrusion). The grip 61 is a hard portion for gripping and rotation manipulating. The grip 61 may enough to have a shape easily manipulate to rotate about the central axis C.

The insertion portion 62 protrudes along with the central axis C from a distal end of the grip 61. The insertion portion 62 has approximately columnar shape. The insertion portion 62 has a size so as to be insertable into the insertion port 51. A base portion 64 having a circular shape is provided between the insertion portion 62 and the grip 61. Lumens for inserting the torque wire 7 are formed in the base portion 64 and the insertion portion 62. The planar portion of the proximal end portion 7*b* of the torque wire 7 is inserted into a distal end plane of the insertion portion 62.

The protrusion 63 protrudes from the outer circumferential surface of the insertion portion 62. In the embodiment, the protrusion 63 elongates toward the distal side from the base portion 64 in the longitudinal direction, and the protrusion 63 is disposed on a proximal portion of the insertion portion 62. As shown in FIG. 7 and FIG. 8, the protrusion 63 is a protrusion piece having an approximately triangle cross-sectional shape in a direction orthogonal to the longitudinal direction. The protrusion 63 is provided such that a vertex 631 of the protrusion 63 elongates in parallel with the longitudinal axis. A slit 65 communicating with an inner circumferential surface of the insertion port 51 is formed in a border portion between the protrusion 63 and an outer circumferential surface 511 of the insertion portion 62. The slit 65 is continuously formed on a distal end of the protrusion 63 and both sides of the protrusion 63 in the circumferential direction. The protrusion 63 is elastically deformed when the protrusion 63 receives an external force. In a natural state that an external force is not applied, the protrusion 63 is kept in a state that the protrusion 63 protrudes from the outer circumferential surface of the insertion portion 62, as shown FIG. 8. The protrusion 63 is deformed radially inward in a case where an external force is applied from outside in the radial direction. In a case where the protrusion 63 is applied an external force in the circumferential direction, the protrusion 63 is slightly deformed. The amount of elastically deformed of the protrusion 63 in the radial direction when applying an external force in the radial direction is larger than the amount of elastically deformed of the protrusion 63 in the radial direction when applying an external force in the circumferential direction.

As shown in FIG. 8, in the example, the two protrusions 63 are arranged on the insertion portion 62 by 180 degree away from each other in a circumferential direction. As shown in FIG. 8, in view from the longitudinal direction, the protrusion 63 protrudes in a direction orthogonal to a flat surface of an end part of the torque wire 7. The protrusion 63 may protrude in a direction along with the flat surface.

The protrusion 63 is configured to be capable of locking with the locking portion 53 in the concave portion 532 of the locking portion 53 of the socket 5. The plurality of concave-convex portions of the locking portion 53 and the protrusion 63 of the rotation handle 6 are meshed with each other, thereby a rotation of the rotation handle 6 relative to the handle main body 2 is controlled. A control mode of the rotation handle 6 relative to the handle main body 2 will be described later.

As described above, the proximal end portion 7*b* of the torque wire 7 is fixed to the rotation handle 6. A distal end portion 7*a* of the torque wire 7 is fixed to the blade 421 of the distal sheath 42. In a state that the treatment tool 1 is arranged straightly in the longitudinal direction, each of the planner portion of the distal end portion 7*a* and the proximal end portion 7*b* of the torque wire 7 are oriented in the same direction. In a case where the rotation handle 6 is manipulated to rotate about the central axis C, a rotation manipulation force of the rotation handle 6 is transmitted via the torque wire 7 to make the blade 421 to rotate, thereby the distal sheath 42 rotates about the central axis C, and the orientation of the incision portion 3 is changed. The orientation of the incision portion 3 is changeable in accordance with a rotation manipulation of the rotation handle 6 about the central axis C.

The treatment tool is switchable between a first configuration and a second configuration. In the first configuration, the rotation handle 6 is freely rotatable relative to the handle main body 2 about the central axis C. In the second configuration, a rotation amount of the rotation handle 6 is restricted when an applied force applied to the rotation handle 6 in a rotation direction of the rotation handle 6 is equal to or less than a predetermined amount, and the rotation handle 6 is rotatable when the applied force is greater than the predetermined amount. The predetermined amount may be 1 cNm. Also, the predetermined amount may be selected from 0.5 to 3 cNm.

FIG. 2, FIG. 3, and FIG. 6 show the treatment tool 1 in the first configuration. In a case where the rotation handle 6 is disposed at a position (second position) where is retracted relative to the handle main body 2, the protrusion 63 is exposed at more proximal side than the insertion port 51 of the socket 5, and the rotation handle becomes the first configuration releasing an engagement of the locking portion 53 with the protrusion 63. In a case where the engagement of the locking portion 53 with the protrusion 63 is released, the rotation handle 6 becomes freely rotatable.

FIG. 4, FIG. 5, and FIG. 8 show the treatment tool 1 in the second configuration. In a case where the rotation handle 6 is disposed at a position (first position) which advances relative to the handle main body 2, positions of the protrusion 63 and the locking portion 53 are matched in the central axis C direction of the rotation handle, thereby the protrusion 63 is locked with the locking portion 53. At this time, the insertion portion 62 is arranged inside the insertion port 51 of the socket 5, and the rotation handle becomes the second configuration that the protrusion 63 is meshed with the locking portion 53. In the second configuration, the insertion portion 62 enters the distal portion of the insertion port 51, and the protrusion 63 is disposed inside the concave portion 532, and the protrusion 64 contacts with a proximal end surface of the convex portion 531. Also, the protrusion 63 is located between the plurality of the convex portions 531. Accordingly, in the second configuration, the protrusion 63 and the locking portion 53 are meshed with each other.

In the second configuration, although a rotation of the rotation handle 6 about the central axis is limited, the rotation handle 6 is rotatable when a force equal to or more the predetermined amount is applied to the rotation handle 6 in the rotation direction. Specifically, when a force equal to or more the predetermined amount is applied to the rotation handle 6 in the rotation direction, a force is applied to the protrusion 63 in the circumferential direction, an inclined surface of the protrusion 63 is pushed in the circumferential direction, thereby the protrusion 63 is elastically deformed and is bent to the central axis C side in the radial direction. When the protrusion 63 is bent equal to or more the predetermined amount, the vertex 631 of the protrusion 63 gets over the convex portion 531 and is capable of moving toward the concave portion 532 adjacent to the convex portion 531 in the circumferential direction. That is, in the second configuration, in a case where a force equal to or more the predetermined amount is applied to the rotation handle 6 in the rotation direction, the protrusion is movable to the adjacent concave portion 532 step by step. In the second configuration, a rotation amount of the rotation handle 6 can be adjusted with a regular amount step by step.

In the second configuration, a click feeling is generated and is fed back to a user grasping the rotation handle 6 (user feedback, second user feedback). Specifically, in a case where a user performs a rotation manipulation of the rotation handle 6 about the central axis C while grasping the rotation handle 6, a vibration in a time when the protrusion 63 gets over the convex portion 531 is transmitted to a hand of a user as a click feeling transmitted to a user, thereby a notice that the rotation handle 6 is rotated with a predetermined amount is fed back to a user. When performing a rotating manipulation of the rotation handle 6, an audible sound is generated in a time when the protrusion 63 gets over the convex portion 531. As described above, in the treatment tool 1, when the rotation handle 6 is rotated with a force equal to or more the predetermined amount is applied to the rotation handle 6 in the rotation direction in a second configuration, a user can recognize a rotation of the rotation handle 6 by the audible sound.

The treatment tool 1 is capable of changing the first configuration and the second configuration. The treatment tool 1 is capable of changing between the first configuration and the second configuration by advancing or retracting the rotation handle 6 relative to the handle main body 2. In the embodiment, the rotation handle 6 is switched to the second configuration by advancing the rotation handle 6 relative to the handle main body 2, and is switched to the first configuration by retracting the rotation handle 6 relative to the handle main body 2 in the second configuration. The rotation handle 6 is switched to the second configuration by advancing the rotation handle 6 in the first configuration.

[Method of Treatment Tool]

An action and a using method of the treatment tool 1 is explained based on an example a procedure using the treatment tool 1.

Figure 29:
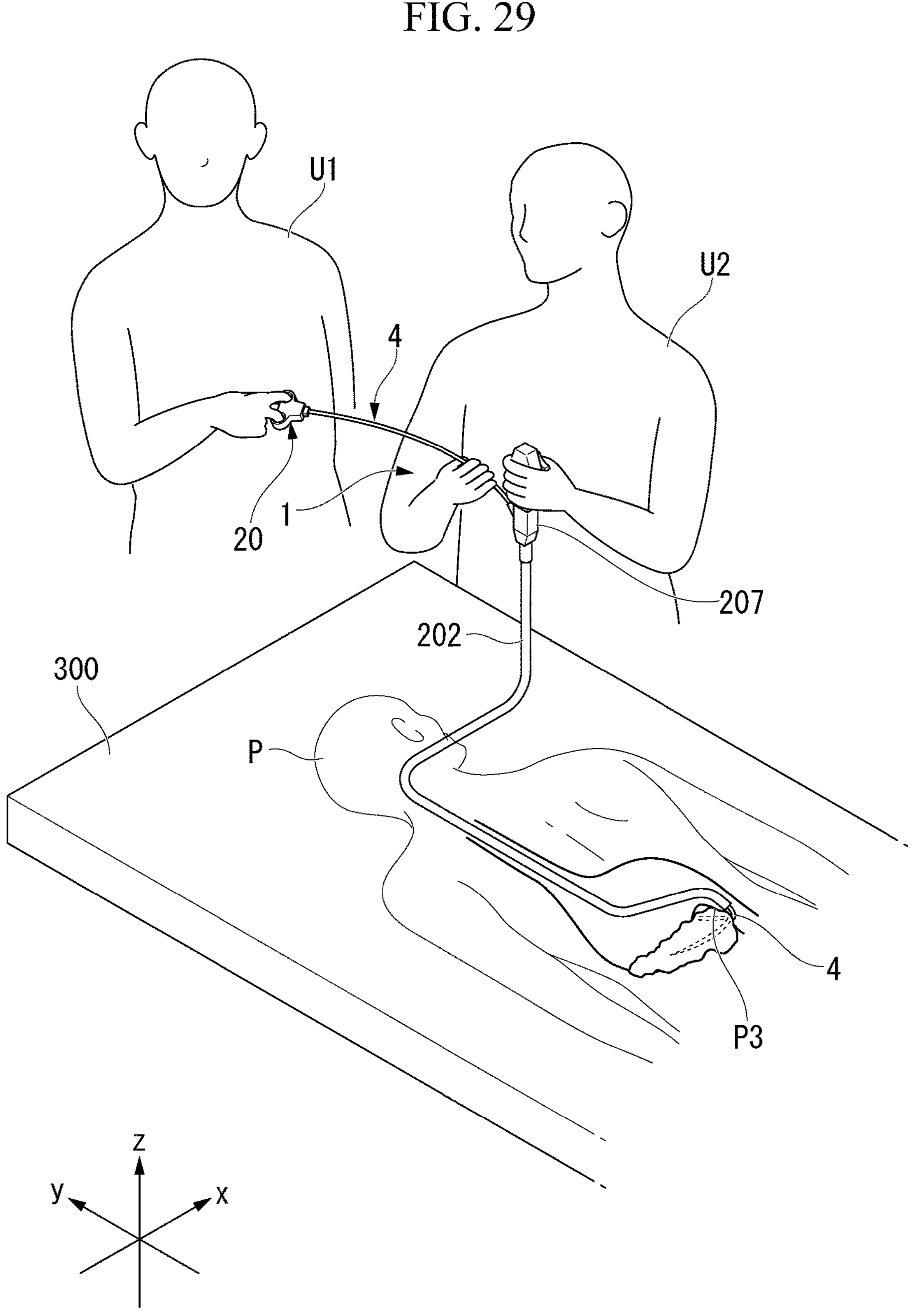
FIG. 29 is a schematic view illustrating the usage mode of the treatment tool according to an embodiment.

In the following procedure, two surgeons U1, and U2 use the treatment system 100 as users. The surgeon U1 holds the operation portion 20 of the treatment tool 1, and the surgeon U2 holds the endoscope operation portion 207 and a part of the sheath 4 of the treatment tool 1. The surgeon U2 inserts the insertion portion 202 from a mouth of a patient P while checking an image displayed on a monitor and also manipulating the input portion 209 to bend the flexible portion 205 as needed. At this time, the patient P lies in a prone position on an examination bed 300 with a face directed rightward as illustrated in FIG. 29.

Though illustration is omitted, a guide wire is inserted into the channel 206 from the forceps port 206*b* and introduced beforehand into the bile duct through the duodenum. The guide wire exposed outside from the forceps port 206*b* is inserted into the guidewire lumen from a distal end portion of the treatment tool 1 and exposed outside from the proximal side of the treatment tool 1. The guide wire is provided over the whole length of the treatment tool 1.

When the insertion portion 202 reaches near the bile duct P3 as a treatment target site from the mouth of the patient P, the sheath 4 of the treatment tool 1 and the flexible portion 205 of the insertion portion 202 are bent at multiple locations. For example, they are bent at a position held by the surgeon U2 after the treatment tool 1 was inserted into the forceps port 206*b*; at a position bent toward the mouth of the patient P when the insertion portion 202 hanging downward from the position of the endoscope operation portion 207 held by the surgeon U2 has reached in the vicinity of an upper surface of the examination bed 300; a position bent along the throat of the patient P; a position bent when they were passed through a stomach ST of the patient P; and a position bent when the distal end portion of the treatment tool 1 was raised by the elevator 212 of the endoscope 200.

The surgeon U2 inserts the sheath 4 into the channel 206 and advances to protrude the sheath 4 from the distal end opening 206*a*.

Here, in a process of advancing the treatment tool 1 toward a treatment target site, as described above, the torque wire 7 is bent at a plurality of positions and twists may occur in the torque wire 7. Accordingly, the rotation handle 6 retracts to transfer from the second configuration to the first configuration, thereby the rotation handle 6 is capable of freely rotating, and a twist of the torque wire 7 is eliminated. The surgeon U2 adjusts an insertion amount of the sheath 4 inserted into the channel 206, and protrudes the distal end of the sheath 4 from the channel 206.

Figure 28:
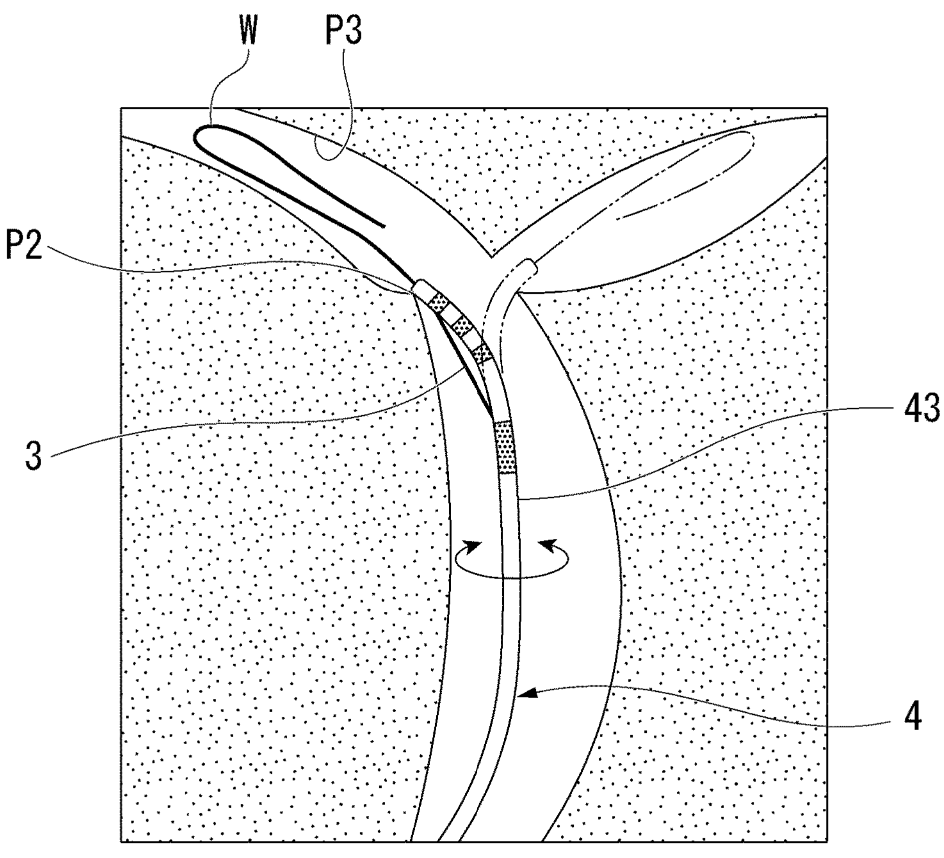
FIG. 28 is a schematic view illustrating the usage mode of the treatment tool according to an embodiment.

Substantially, the rotation handle 6 is advanced relative to the handle main body 2 to switch to the second configuration, and the distal sheath 42 is inserted into the duodenal papilla P2. For example, as shown in FIG. 28, in a case where the orientation of the incising portion 3 is aligned with a target treatment site at the junction of the bile duct and the pancreatic duct or a like site, the rotation handle 6 is rotationally manipulated about the central axis C to adjust the orientation of the incision portion 3. The surgeon U1 applies a force to the rotation handle 6 in the rotation direction while observing the image, the protrusion 63 gets over the convex portion 531 and moved to the adjacent concave portion 532. The rotation manipulation of the rotation handle 6 transferred to a distal side via the torque wire 7 and the distal sheath 42 rotates with a predetermined amount about the central axis C. At this time, a click feeling is fed back to the surgeon U1 (user feedback, second user feedback). The rotation handle 6 is kept in the second configuration after adjusting the orientation of the incision portion 3, and the incision portion 3 is kept in the desired orientation. In the second configuration, the torque wire 7 is allowed to be twisted (the torque wire 7 is kept in twisted). Since the protrusion 63 is capable of being kept in an engaging with the locking portion 53 when the rotation handle 6 is rotationally manipulated in the second configuration, the rotation handle 6 maintains a state that the incision portion 3 is aligned with the desired orientation while allowing a twist of the torque wire 7.

The surgeon U1 checks the site of an encircling fold P4 in an image imaged by the imaging portion 203 to determine an incising direction, and checks the current orientation of the incising portion 6. The surgeon U1 determines a direction to be incised and adjusts the orientation of the incision portion 3 with the 12 o'clock direction in the image by rotationally manipulating the rotation handle 6 in the second configuration about the central axis. In the state, the elevator 212 is moved to bend the distal sheath 42 by manipulation of the surgeon U2, thereby the treatment tool 1 is capable of protruding the distal sheath 42 in a state that the distal sheath 42 is oriented to a direction approximately with a direction to be incised.

If the position of the encircling fold P4 of the patient P is offset from the 12 o'clock direction in the image, the surgeon U2 changes the orientation of the incising portion 3 to the 11 o'clock direction in the image, as will be described hereinafter.

The surgeon U2 rotates the rotation handle 6 about the central axis C and makes a proximal end portion 7*b* of the torque wire 7 to rotate with a predetermined amount in one side of the circumferential direction.

A rotation torque is transferred to the blade 421 via the torque wire 7, and transferred to the distal sheath 42. Thereby, a rotation torque input in the rotation handle 6 by the surgeon U1 is transmitted to the distal sheath 42 via the torque wire 7, and the incision portion 3 rotates about the central axis C.

While rotating the rotation handle 6 to cause a rotational torque to act on the sheath 4 via the torque wire 7 and observing the orientation of the distal sheath 42 about the longitudinal axis C on the image, the surgeon U1 brings the orientation of the incising portion 3 into alignment with the 11 o'clock direction in the image. As described hereinbefore, in the treatment tool 1, the orientation of the incising portion 3 can be adjusted even if the direction to be incised is different from the 12 o'clock direction in an image due to an individual difference among patients. At this time, if the rotation handle 6 is manipulated in the second configuration, the orientation of the incision portion 3 can be changed little by little. If the rotation handle 6 is manipulated in the second configuration, the incision portion 3 is capable of being kept in a state that the incision portion 3 adjusted in the desired orientation.

Substantially, the terminal 74 of the treatment tool 1 is connected to the high-frequency power source. The surgeon U2 retracts the handle shaft 81 relative to the slider 82 of the knife handle 8 to make the incising portion 3 taut. A high-frequency current is supplied from the high-frequency power source, and the elevator 212 is manipulated to raise and lower so that the distal sheath 42 is caused to perform a swinging motion. To the tissue of the duodenal papilla P2 with which the incising portion 3 has been maintained in contact, the high-frequency current and a pressure produced by a tension of the incising portion 3 are applied so that the duodenal papilla P2 is incised. If the necessary length of incision is successfully confirmed to have reached based on an image on the monitor, for example, the supply of the high-frequency current is stopped.

After completion of the incision of the duodenal papilla P2, the slider 82 is pushed in to cause the incising portion 3 to lie along the distal sheath 42, and the treatment tool 1 is then pulled out from the channel 206. At this time, an unillustrated basket forceps or the like is inserted into the channel 206 in place of the treatment tool 1. The basket forceps is inserted from the incised duodenal papilla P2 into the bile duct P3 to capture stones. The stones are removed from the bile duct P3. After the removal of the stones, the basket forceps and endoscope 200 are pulled out of the body, the procedure is terminated.

According to the treatment tool 1 according to the present embodiment, a rotation of the rotation handle 6 is limited in the second configuration. Since the circumferential direction of the rotation handle 6 relative to the handle main body 2 is maintained in a predetermined portion, a state that the orientation of the incision portion 3 is adjusted is maintained. Consequently, the incision portion is maintained their orientation on approximately to a desired position even if the orientation of the incision portion 3 is unintentionally changed in accordance with an occurrence of twist of the sheath 4 or the torque wire 7 on an insertion route of the treatment tool 1. Furthermore, in the second configuration, the rotation handle 6 rotates with a predetermined rotation amount when a force equal to or more the predetermined amount is applied to the rotation handle 6 in the rotation direction. Therefore, when the orientation of the incision portion 3 is adjusted, the treatment tool 1 is capable of adjusting the orientation of the incision portion 3 while preventing the orientation of the incision portion 3 from dramatically changing due to twists of the sheath 4 or the torque wire 7.

According to the treatment tool 1 according to the present embodiment, the first configuration and the second configuration are capable of changing by a simple operation such that the rotation handle 6 advances and retracting relative to the handle main body 2.

According to the treatment tool 1 according to the present embodiment, since the rotation handle 6 is freely rotatable in the first configuration, if a distal part of the torque wire 7 is twisted, the user grasping the rotation handle 6A receive a reaction force generated due to a twist or the like in the torque wire 7, and the user obtained a feeling that a rotation of the rotation handle 6 is pushed back in the reverse direction (first user feedback). Since the rotation handle 6 rotates freely, if a twist occurs in the distal side of the torque wire 7, the user releases the rotation handle 6 in the first configuration by hand, then the rotation handle 6 rotates freely to eliminate the twist of the torque wire 7. Consequently, a twist of the torque wire 7 is capable of easily being eliminated.

Hereinafter, a modified example of the treatment tool 1 will be described. In the following description, configurations common to the previous description will be assigned the same reference signs, and a description thereof will be omitted.

Modified Example 1

Figure 9:
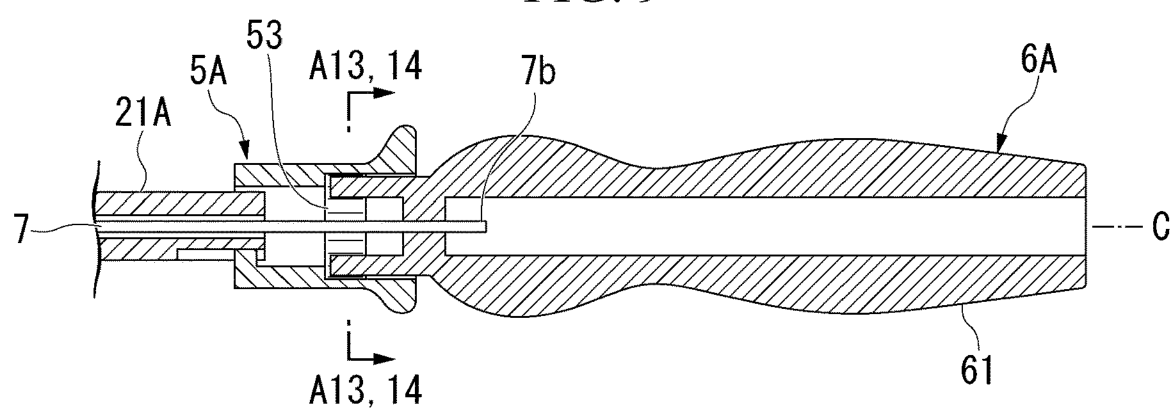
FIG. 9 is a cross-sectional view of the rotation handle of the modified example 1 in a longitudinal direction.

The treatment tool of the modified example 1 will be described with reference to FIG. 9 to FIG. 14. The above embodiment shows an example that the first configuration and the configuration are switched by advancing and retracting the rotation handle 6 relative to the handle main body 2. A structure for changing between the first configuration and the configuration is not limited the example. In the present modified example, the handle main body, the socket, and the rotation handle are different from the above embodiment. FIG. 9 and FIG. 11 are cross-sectional views of the vicinity of the rotation handle 6A and the connection portion 21A of the modified example 1 in a longitudinal direction. FIG. 9 shows the second configuration and FIG. 11 shows the first configuration.

Figure 11:
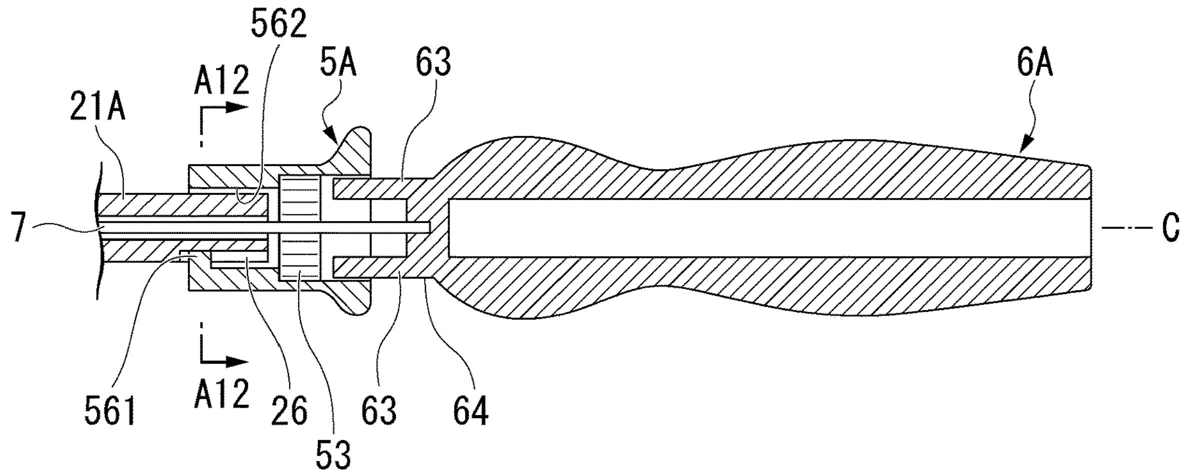
FIG. 11 is a cross-sectional view of the rotation handle of the modified example 1 in a longitudinal direction.
Figure 12:
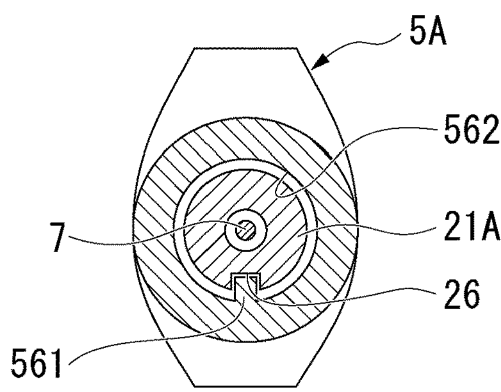
FIG. 12 is a vertical cross-sectional view in A12-A12 line shown in FIG. 11.

The socket 5A and the connection portion 21A of the handle main body 2 are separate members. The socket 5A is attached to the handle main body 2 so as to be capable of being advanced and retracted relative to the connection portion 21A. A groove 26 extending from the proximal end of the connection portion 21A along the longitudinal direction is formed on an outer circumferential surface of the connection portion 21A. The socket 5A includes an insertion passage 562 and a sliding portion 561. A proximal end of the connection portion 21 is inserted into the insertion passage 562. As shown in FIG. 12, the sliding portion 561 is configured to which a part of an inner circumference surface of the insertion passage 562 in the circumferential direction is protruded inward. The sliding portion 561 enters the groove 26 and is slidable in the groove 26 in the longitudinal direction. As shown in FIG. 9 and FIG. 11, the locking portion 53 is formed on an inner circumference surface 511 of the distal end portion of the insertion port 51 of the socket 5A.

Figure 10:
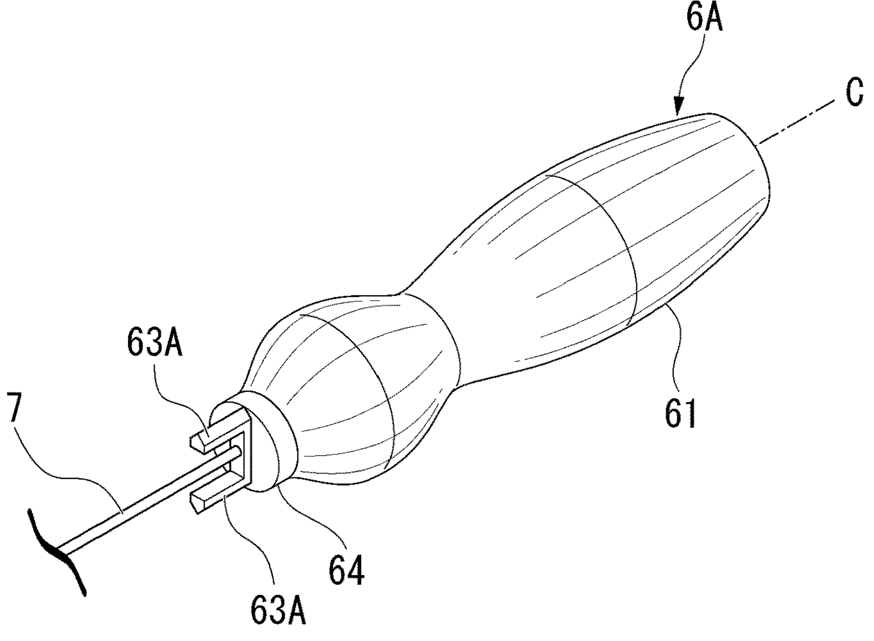
FIG. 10 is a perspective view of the rotation handle of the modified example 1.

As shown in FIG. 10, the configuration of a distal end portion of the rotation handle 6A is different from the above embodiment. The protrusion 63A is provided to protrude from a distal end surface of the base portion 64 toward the distal side and parallel with the central axis C. A cross-sectional shape of the protrusion 63A in a direction orthogonal to the longitudinal direction is the same as the above embodiment.

Figure 13:
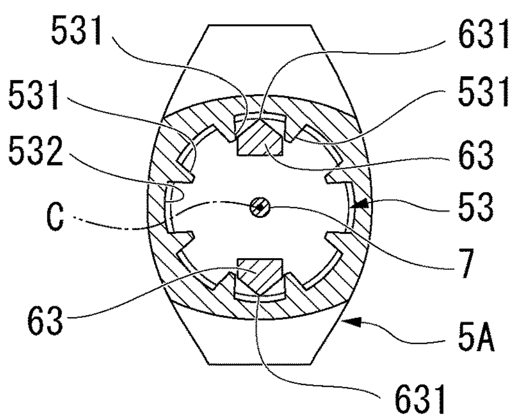
FIG. 13 is a vertical cross-sectional view in A13-A13 line shown in FIG. 9.
Figure 14:
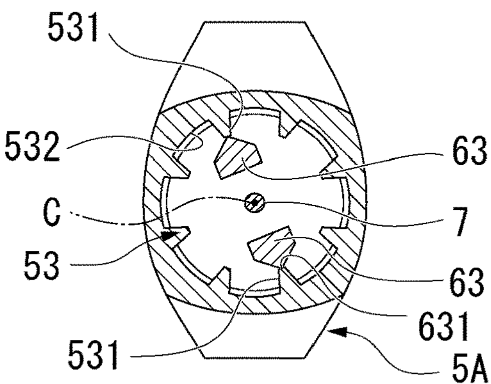
FIG. 14 is a vertical cross-sectional view in A14-A14 line shown in FIG. 9.

The sliding member 561 of the socket 5A is inserted into the groove 26, and a proximal end portion of the connection portion 21 is inserted into the insertion passage 562. The socket 5A advances and retracts relative to the connection portion 21 while sliding the sliding portion 561 in the groove 26. A position of the rotation handle 6A in the longitudinal direction relative to the handle main body 2 is fixed. As shown in FIG. 9, when the socket 5A is arranged at a retracted position, the protrusion 63A is inserted into the insertion port 51 of the socket 5A and the protrusion 63A is locked with the locking portion 53, thereby the rotation handle 6A is set in the second configuration. In the second configuration, as shown in FIG. 13 and FIG. 14, the protrusion 63A is locked with the locking portion 53, a force equal to or more the predetermined amount is applied to the rotation handle 6A in the rotation direction in the same manner as the first embodiment, thereby, the rotation handle 6A rotates with the predetermined amount. At this time, a user feels a click feeling (user feedback, the second user feedback) in the same manner as the first embodiment. As shown in FIG. 11, the socket 5A advances relative to the connection portion 21, the rotation handle 6A is switched to the first configuration. In the first configuration, the sliding portion 561 of the socket 5A in contacts with a distal end of the groove 26, the protrusion 63A is arranged inside the insertion port 51 positioned at a proximal side than the locking portion 53, an engagement of the protrusion 63A with the locking portion 53 is released, and the rotation handle 6A becomes freely rotatable. In the first configuration, the user grasping the rotation handle 6A receive a reaction force generated due to a twist or the like in the torque wire 7, and the user obtained a feeling that a rotation of the rotation handle 6A is pushed back in the reverse direction (first user feedback).

According to the treatment tool according to the modified example, the first configuration and the configuration are switched by advancing and retracting the socket 5A relative to the rotation handle 6A and the handle main body 2 in the longitudinal direction.

Modified Example 2

The treatment tool of the modified example 2 will be described with reference to FIG. 15 to FIG. 18. The socket and the rotation handle may be locked with each other via the protrusion and the locking portion. For example, the modified example shown in FIG. 15 and FIG. 16, the rotation handle 6B may be provided with the plurality of concave-convex portions, and the protrusion may be provided on an inner circumferential surface of the socket 5B. The socket 5B and the connection portion 21A of the modified example 2 are separately constituted in the same manner as the modified example 1. The socket 5B is attached so as to be capable of advancing and retracting in the longitudinal direction and so as to be non-rotatable relative to the connection portion 21A. The socket 5B advances and retracts in the longitudinal direction by sliding the sliding portion 561 in the groove 26. As shown in FIG. 16, a protrusion 58 is provided in the socket 5B. The protrusion 58 protrudes from an inner circumferential surface of the insertion port 51 toward a radially inside. Two slits 581 are formed in a portion providing the protrusion of the socket 5B so as to apart from each other in the circumferential direction. The slits 581 elongate from a proximal end of the socket 5B toward the distal side in the longitudinal direction. As the result of forming the slits 581, the protrusion 58 is bent in the radial direction when an external force is applied to the protrusion 58. A plurality of concave-convex portions are formed on an outer circumferential surface of the base portion 64 of the rotation handle 6B to form a locking portion 66. The protrusion 58 is locked with the locking portion 66.

Figure 15:
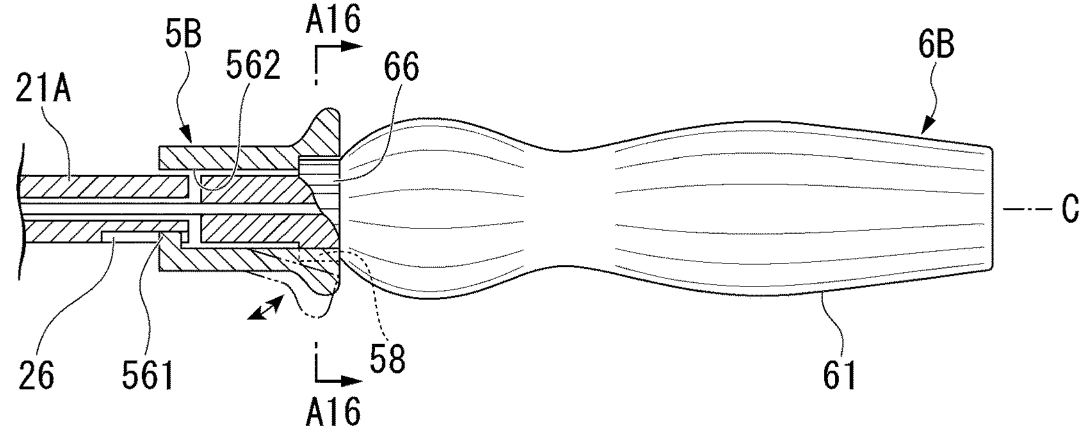
FIG. 15 is a partial cross-sectional view of the rotation handle of the treatment tool of the modified example.
Figure 16:
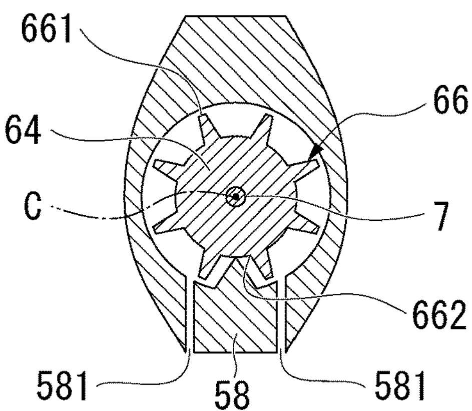
FIG. 16 is a vertical cross-sectional view in A16-A16 line shown in FIG. 15.
Figure 17:
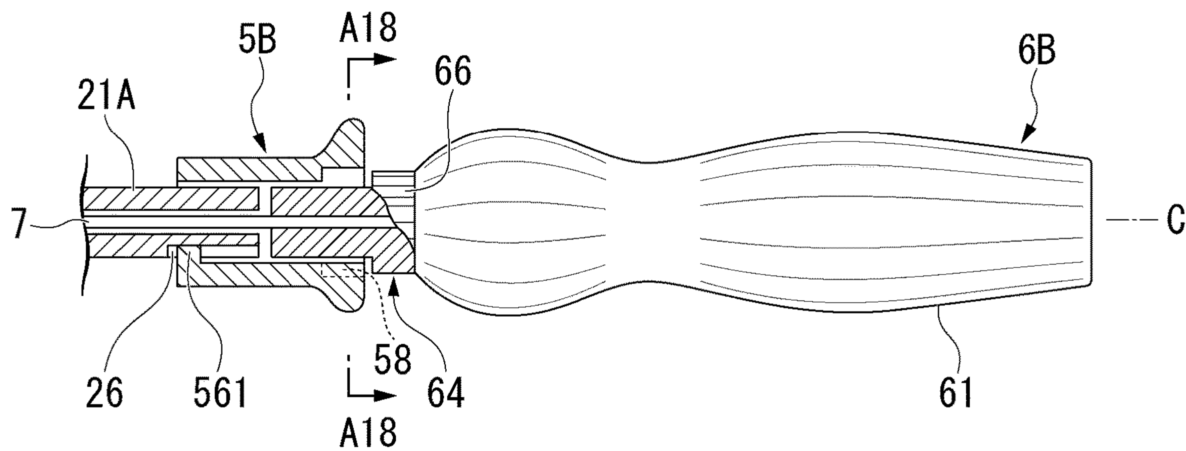
FIG. 17 is a partial cross-sectional view of the rotation handle of the treatment tool of the modified example.
Figure 18:
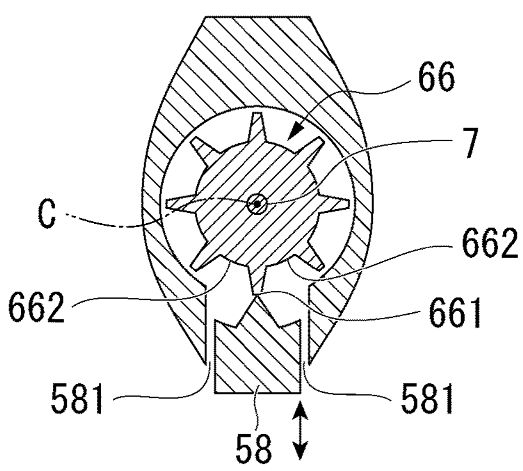
FIG. 18 is a cross-sectional view in A18-A18 line shown in FIG. 17.

FIG. 15 shows a region of the rotation handle 6B and the connection portion 21 in the second configuration. FIG. 17 shows a region of the rotation handle 6B and the connection portion 21 in the first configuration. In the second configuration, the socket 5B is arranged at a retracted position relative to the connection portion 21. When the socket 5B is arranged at the retracted position, the protrusion 58 is positioned and locked in the concave portion 662 of the locking portion 66. In a case where the rotation handle 6B is rotated in the second configuration, as shown in FIG. 18, the protrusion 58 is in contact with the convex portion 661 of the locking portion 66 to make the protrusion 58 to be bent toward a radially outside, the protrusion 58 gets over the convex portion 661 and respectively moved to an adjacent concave portion 662, and the protrusion 58 is locked again. At this time, a user feels a click feeling (user feedback, the second user feedback). In the first configuration, the socket 5B is arranged at an advanced position relative to the connection portion 21. In the first configuration, the locking portion 53 is exposed at more proximal side than the insertion port 51 of the socket 5B, and an engagement of the locking portion 53 with the protrusion 58 is released. The rotation handle 6B freely rotates in the first configuration. In the first configuration, a user feels a reaction force generated due to a twist or the like in the torque wire 7 (first user feedback).

Second Embodiment

The treatment tool 1C according to the second embodiment will be described with reference to FIG. 19 to FIG. 23. In the following description, configurations common to the previous description will be assigned the same reference signs, and a description thereof will be omitted.

The treatment tool 1C according to the embodiment is an example in which the configuration of the operation portion is different from the first embodiment. The operation portion 20C according to the embodiment does not include the knife handle 8, and a rotating manipulation and a manipulation for the incision portion is performed by only the handle 6C. The operation portion 20C includes the handle main body 2C and the handle 6C.

The handle main body 2C does not include two connection portions 21, and 22 branched in the handle main body 2 of the first embodiment. A proximal end portion 23 of the handle main body 2C straightly elongates in the longitudinal direction. A coupling portion 861 to the handle 6C is provided at an outer circumferential portion of the proximal end portion 23. A liquid supply port 29 is provided on the proximal end portion 23 of the handle main body 2C. An unillustrated syringe can be detachably attached to the fluid supply port 29. The liquid supply port 29 communicates with a lumen 231 of the handle main body 2C. An operation wire 7C is inserted into the lumen 231 of the handle main body 2C. The lumen 231 also functions as a liquid supply lumen.

The handle 6C includes a handle shaft 61C, a slider 62C, a terminal port 68, and a socket 5C. The handle shaft 61C is attached to the proximal end portion 23 of the handle main body 2C. The coupling portion 862 is provided at a distal end of the handle shaft 61C. Due to a coupling the coupling portion 861 of the handle main body 2C with the coupling portion 862 of the handle shaft 61C, the handle shaft 61C is coupled with the handle main body 2C such that the handle shaft 61C is immovable in the longitudinal axis direction and is rotatable about the central axis C relative to the handle main body 2C. A locking portion 67 is provided on an outer circumference surface of the handle shaft 61C at a proximal side than the coupling portion 862. The locking portion 67 consists of a plurality of concave-convex portions. The locking portion 67 has a constitution which is the same as the locking portion 66 of the modified example 2 as shown in FIG. 15.

The slider 62C is provided so as to be advanceable and retractable relative to the handle shaft 61C in the longitudinal direction. The slider 62C is provided so as to be freely slidable relative to the handle shaft 61C. The slider 62C is engaged with the handle shaft 61C so as to be advanceable and retractable, and to be non-rotatable relative to the handle shaft 61C. The slider 62C has a constitution which is the same as the slider 82 of the knife handle 8 of the first embodiment. The terminal port 68 is provided in the slider 62C.

The operation wire 7C is a wire made of a conductive material and having a torque transmission performance. The incision portion 3 (electrode) is coupled to a distal end portion of the conductive wire 72. The incision portion 3 is capable of protruding from the distal end of the sheath 4. For example, the operation wire 7C is covered with the insulating material except for the incision portion 3 on the distal end portion. That is, the operation wire 7C has functions of the conductive wire 72 and the torque wire 7 of the first embodiment. The terminal 74 is provided on a proximal end portion of the operation wire 7C in the same manner as the conductive wire 72 of the first embodiment.

A proximal end portion of the operation wire 7C passes through a lumen 231 of the handle main body 2C, inserted into the handle shaft 61C, elongated to a vicinity of the terminal port 68, and connected to the terminal 74. The terminal 74 is provided inside the terminal port 68 and fixed to the slider 62C. The terminal 74 is capable of connecting to an external high-frequency power source. In the same manner as the knife handle 8 of the first embodiment, in a case where the slider 62C advances relative to the handle shaft 61C, it can be in a state that the incision portion 3 is in an approximately straight and the incision portion 3 is made to be disposed along with the outer circumferential surface of the distal sheath 42. In a case where the slider 62C retracts relative to the handle shaft 61C, the distal sheath 42 is relatively bent so that the incising portion 3 can be brought into a taut state.

The socket 5C has a constitution which is the same as the socket 5B of the modified example 2 as shown in FIG. 15. The socket 5C is attached so as to be capable of advancing and retracting in the longitudinal direction and so as to be non-rotatable relative to the proximal end portion 23 of the handle main body 2. The coupling portion 86 coupling the handle main body 2 with the handle shaft 61C is arranged inside the insertion port 51 of the socket 5C.

Figure 19:
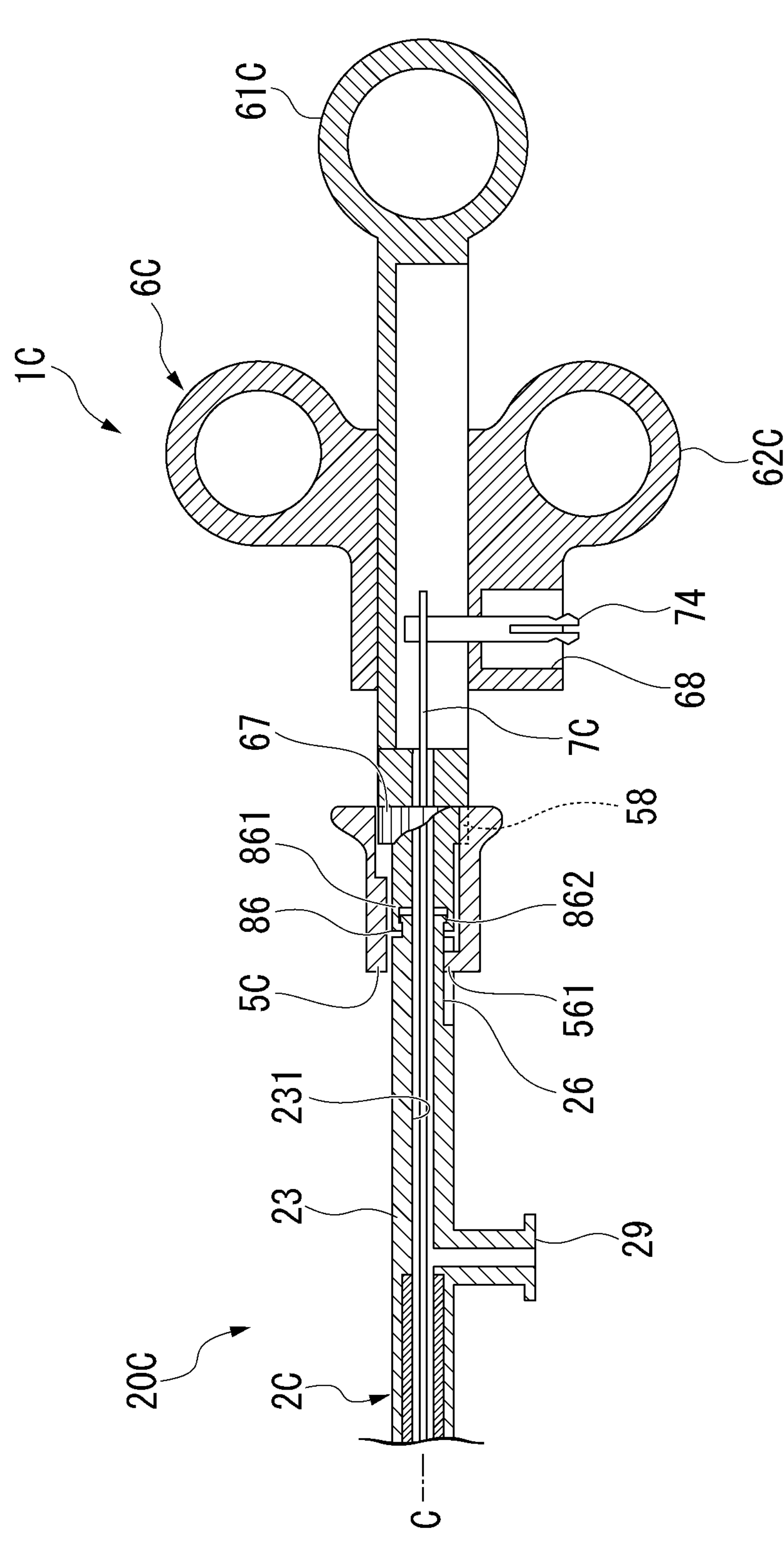
FIG. 19 is a cross-sectional view of a handle of the second embodiment in a longitudinal direction.
Figure 20:
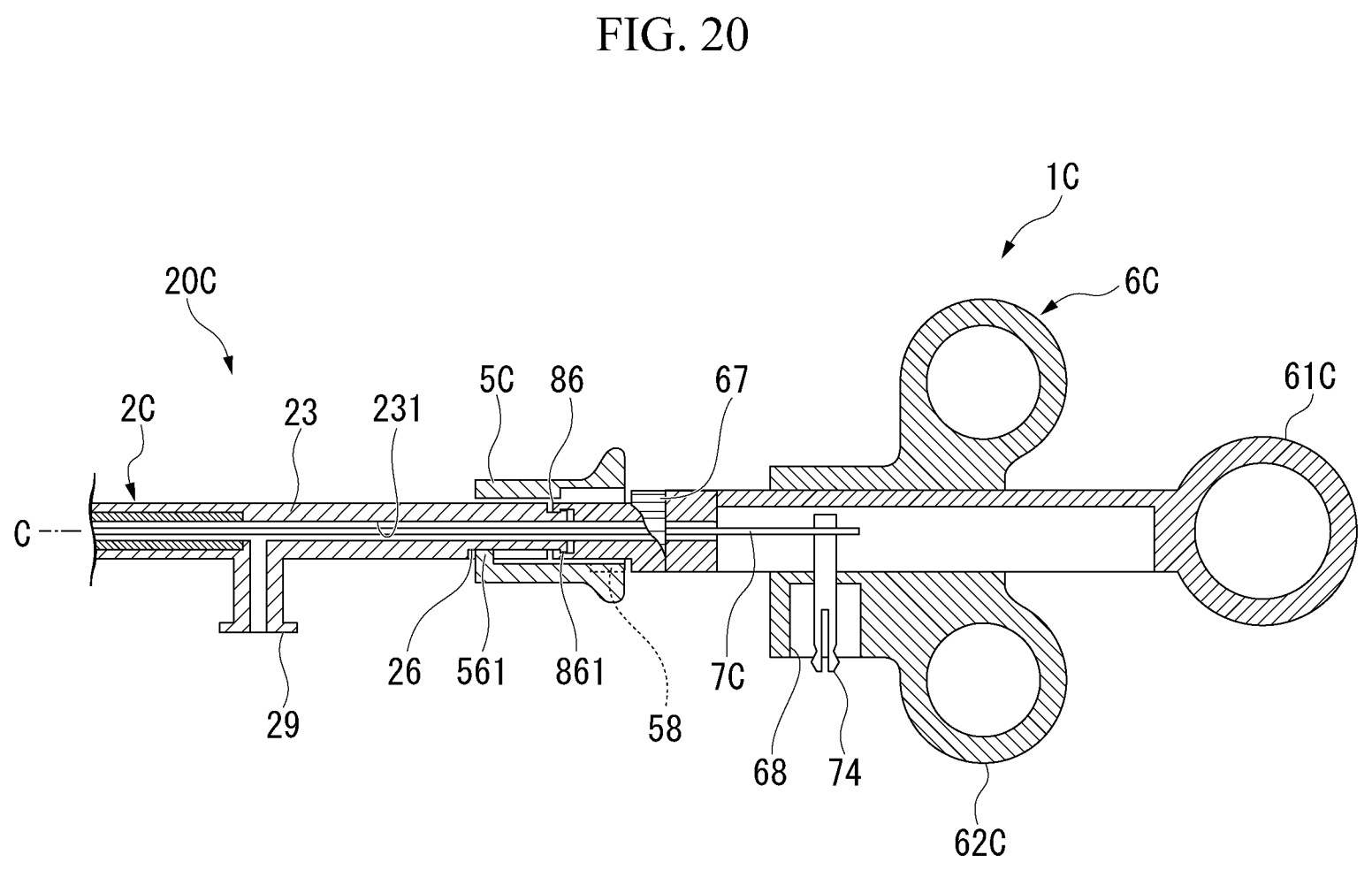

FIG. 19 shows the operation portion 20C in the second configuration and FIG. 20 shows the operation portion 20C in the first configuration. In a case where the socket 5C is disposed at a position where is advanced relative to the handle main body 2C, the rotation handle becomes the first configuration. In a case where the socket 5C is disposed at a position where is retracted relative to the handle main body 2C, the rotation handle becomes the first configuration. In the first configuration shown in FIG. 20, an engagement of the protrusion 58 with the locking portion 67 is released in the same manner as the above modified example 2. In the first configuration, the handle shaft 61C is capable of rotating relative to the handle main body 2 about the central axis C. In the first configuration, a user grasping the rotation handle 61C receive a reaction force generated due to a twist or the like in the torque wire 7C, and the user obtained a feeling that a rotation of the handle shaft 61C is pushed back in the reverse direction (first user feedback). The second configuration shown in FIG. 19, the protrusion 58 is locked with the locking portion 67 by retracting the socket 5C. In the second configuration, a rotation of the handle shaft 61C relative to the handle main body 2 is restricted. Same as a constitution of the modified example 2, when a force equal to or more the predetermined amount is applied to the handle shaft 61C in the rotation direction, the protrusion 58 of the socket 5C gets over the convex portion of the locking portion 67, and moves to the adjacent concave portion. It is also in the treatment tool 1C according to the embodiment, in the second configuration, in a case where a user rotates the handle shaft 61C with a force equal to or more the predetermined amount, a user feels a click feeling (user feedback, the second user feedback).

According to the treatment tool 1C according to the present embodiment, the handle 6C is switched between the first configuration and the configuration by a simple manipulation such that the socket 5C advances and retract in the longitudinal direction. In the first configuration, the handle shaft 61C is freely rotatable relative to the handle main body 2C. As the result, when a procedure using the treatment tool 1C, if a twist occurs in the operation wire 7C due to a plurality of bending in a route of the sheath 4, a user moves the socket 5C to switch to the first configuration, thereby the handle shaft 61C becomes freely rotatable, and the twist of the operation wire 7C can be eliminated.

Although the second embodiments have been described above, the technical scope of the present disclosure is not limited to the above-described embodiments, the specific configuration is not limited to the embodiment and includes design changes and the like within a range not deviating from the gist of the present disclosure. The components shown in the above-described embodiment and the modifications shown below can be appropriately combined and configured.

Modified Example 3

Figure 21:
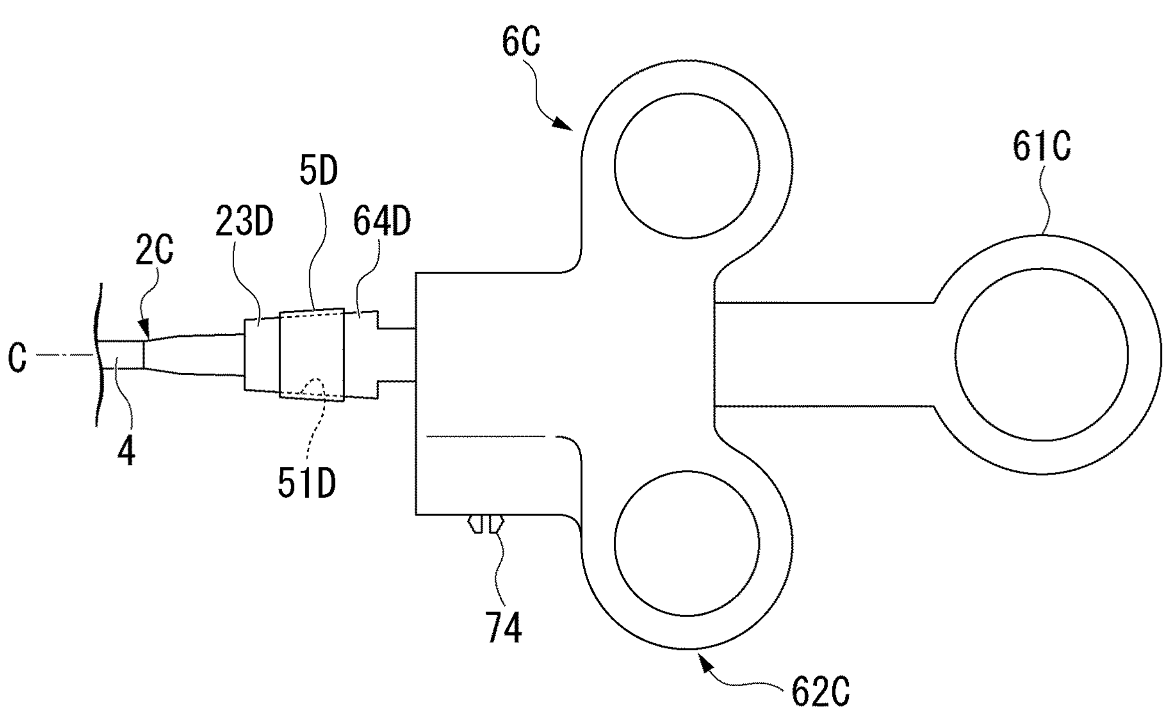
FIG. 21 is a side view of the handle according to the second embodiment.
Figure 22:
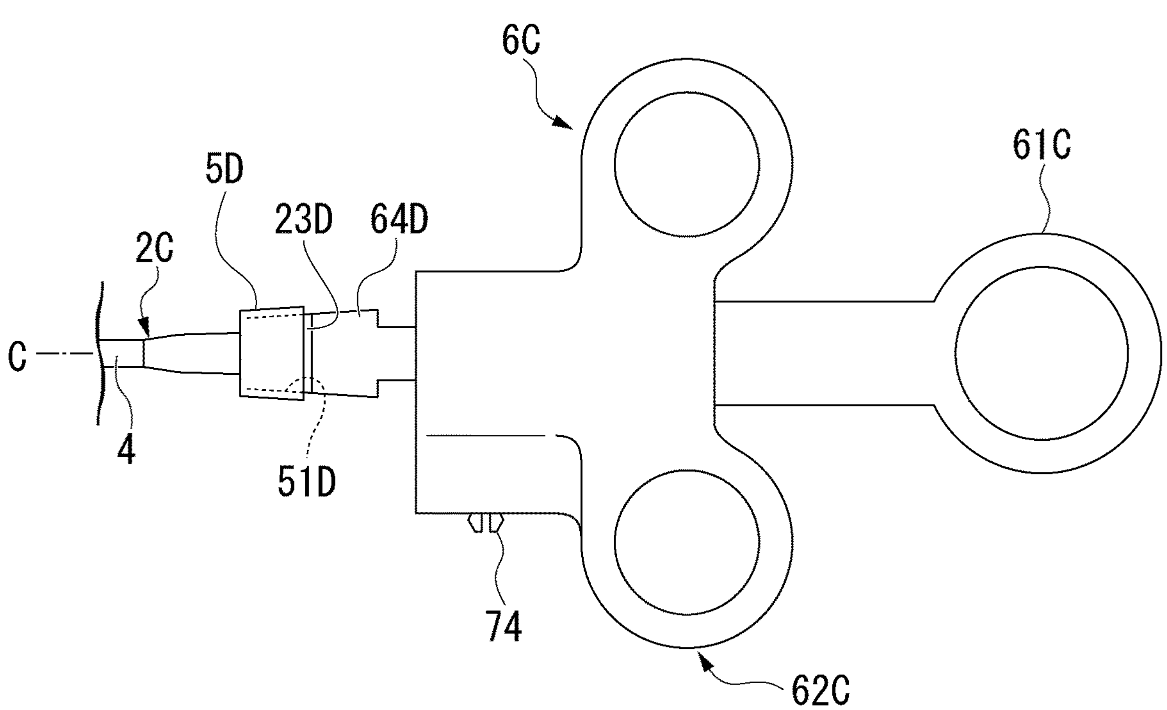
FIG. 22 is a side view of the handle.

The second embodiment shows an example that the socket 5C and the handle shaft 61C are locked with each other via the protrusion 58 of the socket 5C and the locking portion 67 including a plurality of concave-convex portions. Means for switching between the first configuration and the configuration is not limited the above example. For example, a constitution of a modified example 3 shown in FIG. 21 and FIG. 22 may be adopted. FIG. 21 shows the handle 6C in the first configuration, and FIG. 22 shows the handle 6C in the second configuration. In this modified example, in the same manner as the second embodiment, the handle main body 2C and the handle shaft 61D are coupled with each other via the coupling portion 86 so as to be rotatable and not to advance and retract. The handle shaft 61D does not include a locking portion at the distal end thereof, and the socket 5D does not include the protrusion 58. As shown in FIG. 21 and FIG. 22, both an outer circumferential surface of a proximal end portion 23D of the handle main body 2C and an outer circumferential surface of a distal end portion 64D of the handle shaft 61C form a tapered plane being radially expand as going toward a proximal side. The socket 5D is a ring-like member having a cylindrical insertion port 51D which has similar shape to the tapered shape of the outer circumferential surfaces of the handle main body 2C and the handle shaft 61C. The socked 5D is provided so as to be advanceable and retractable relative to the handle main body 2C and the handle shaft 61C in the longitudinal direction.

Since an inner diameter of the insertion port 51 of a proximal end of the socket 5D is larger than an outer diameter of a distal end portion of the handle shaft 61C, when the socket 5D is shifted to the distal side, as shown in FIG. 22, a gap between the socket 5D and the handle shaft 61C appears. As the result, a lock of the handle shaft 61C with the handle main body 2C in the circumferential direction is released to switch to the first configuration in which the handle shaft 61C is freely rotatable. As shown in FIG. 21, if the treatment tool has a constitution in which a distal end portion of the handle shaft 61C is exposed when the socket 5D is arranged to the distal side, a user easily recognizes that it has been switched to the first configuration. As shown in FIG. 22, when the socket 5D is arranged to the proximal side, an outer circumferential surface of the handle shaft 61C and an inner circumferential surface of the socket 5D are frictional engaged with each other. At the same time, an outer circumferential surface of the handle main body 2C and the inner circumferential surface of the socket 5D are frictional engaged with each other. As a result, the handle main body 2C and the handle shaft 61C are locked via the socket 5D in a rotatable state.

A constitution for switching a relative rotation of the handle main body 2C and the handle shaft 61C by the socket 5D is not limited the frictional engagement. For example, locking portions including grooves and protrusions are provided on the handle main body 2C, the handle shaft 61C, and the socket 5D may be adapted.

Figure 23:
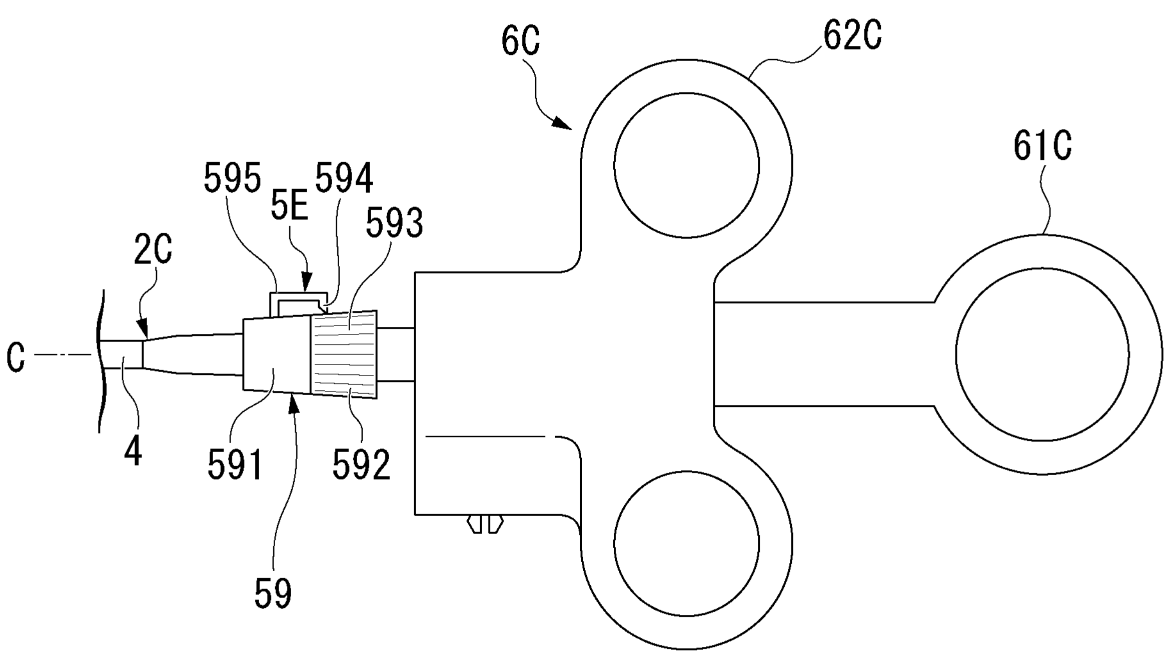
FIG. 23 is a side view of the handle of the treatment tool of a modified example of the second embodiment.
Figure 24:
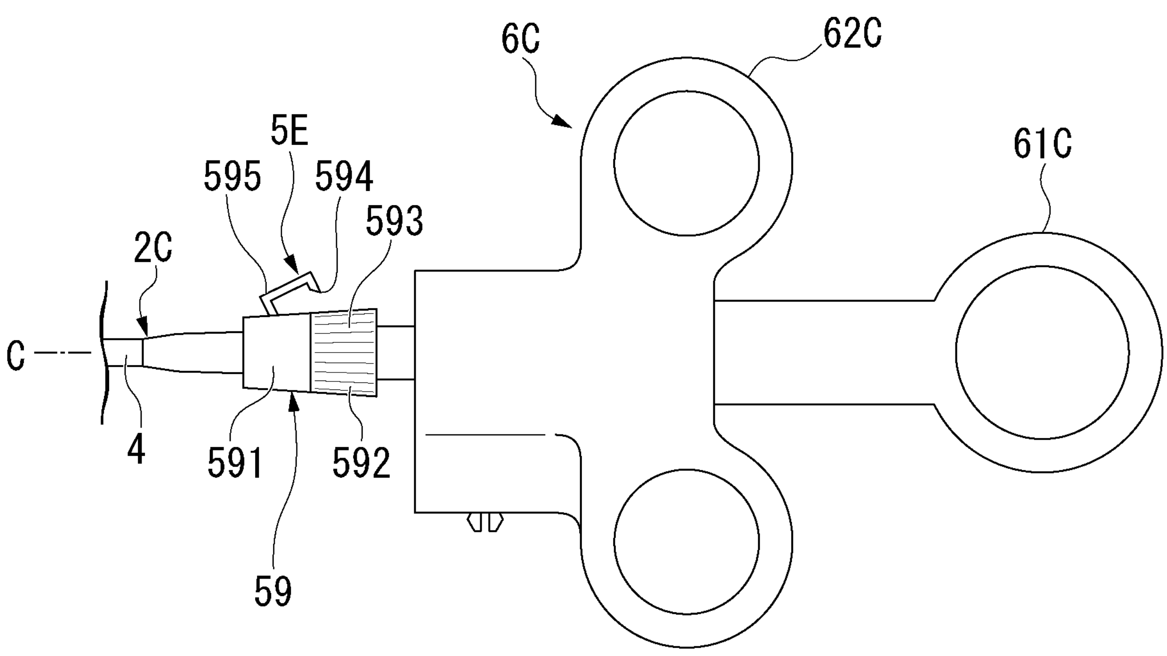
FIG. 24 is a side view of the handle of the treatment tool of a modified example of the first embodiment.

Furthermore, as shown in FIG. 23 and FIG. 24, a locking portion 59 may be provided on an outer circumference portion of a socket 5E. The socket 5E includes a distal end member 591 disposed on the handle main body 2C side, and a proximal member 592 disposed on the handle shaft 61C side. The distal member 591 and the proximal member 592 are contacted with each other in the longitudinal direction, and an outer shape of the distal member 591 and the proximal member 592 in a contacted state is a substantially truncated cone shape. A locking portion 593 constituting a plurality of concave-convex portions are formed on an outer circumferential surface of the proximal member 592. A protrusion 594 is provided on an outer circumferential portion of the distal end portion 591. The protrusion 594 is attached to the outer circumferential portion of the distal end portion 591 via an arm 595. The protrusion 594 is configured to move in a radial direction of the distal end member 591.

FIG. 23 shows an operation portion 20E in the second configuration, and FIG. 24 shows the operation portion 20E in the first configuration. As shown in FIG. 23, in the second configuration, the protrusion 594 is locked with the locking portion 593, and a rotation of the handle shaft 61C relative to the handle main body 2C is limited. As shown in FIG. 24, in the first configuration, the arm 595 is separated outward from the socket 5E in the radial direction, and an engagement of the protrusion 594 with the locking portion 593 is released, and the handle shaft 61C becomes freely rotatable. The arm 595 is moved by hand to engage and release the engagement of the protrusion 594 with the locking portion 593. According to the modified example, the first configuration and the configuration is capable of being switched by rotating the socket 5E about the central axis C.

For example, the protrusion 594 may have a constitution that is movable in the radial direction by elastically deforming the arm 595. For example, the protrusion 594 may have a constitution that the arm 595 is rotatably attached to a distal member 591 and the protrusion 594 may be rotatable in the radial direction.

Figure 25:
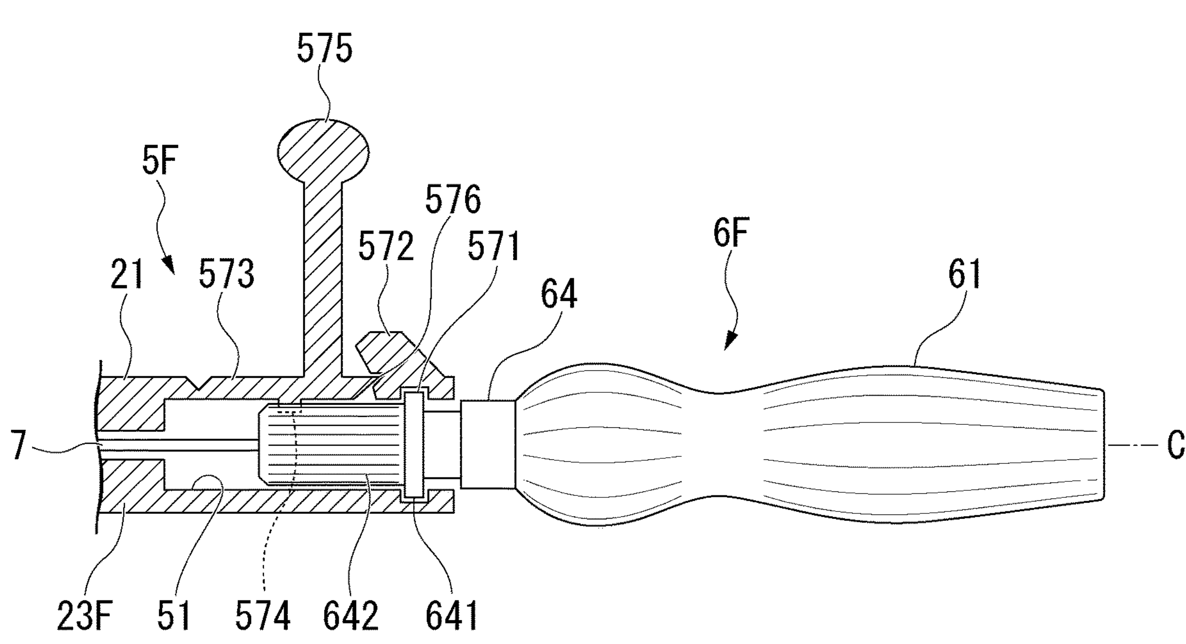
FIG. 25 is a partial cross-sectional view of the handle of the treatment tool of a modified example of the second embodiment.
Figure 26:
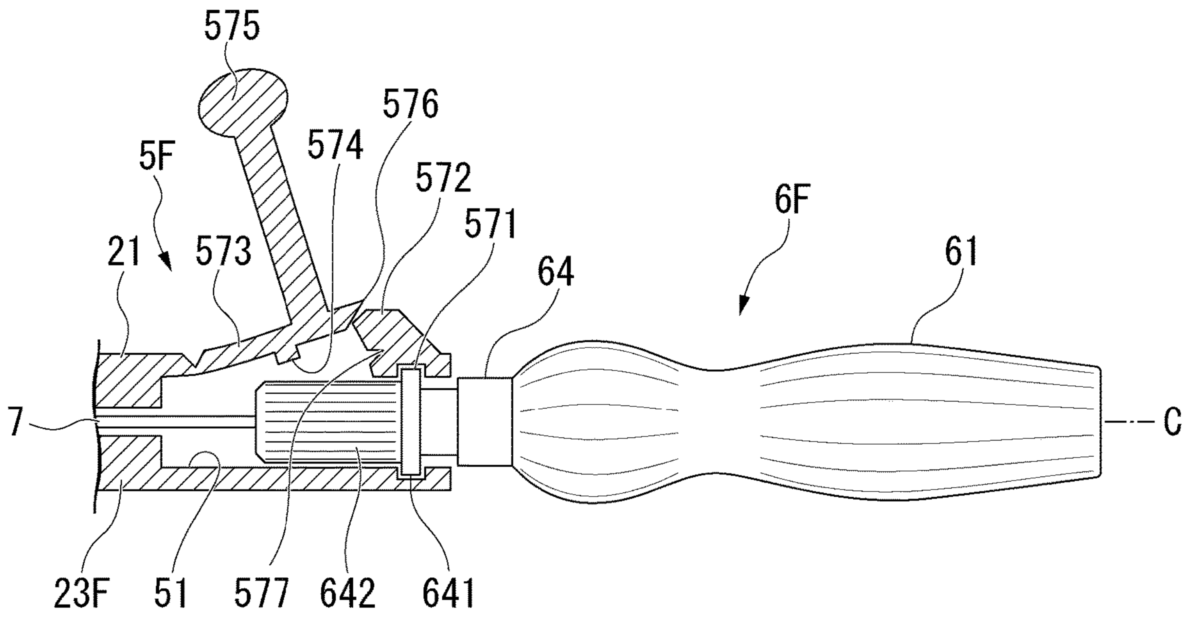
FIG. 26 is a partial cross-sectional view of the handle of the treatment tool of a modified example of the second embodiment.
Figure 27:
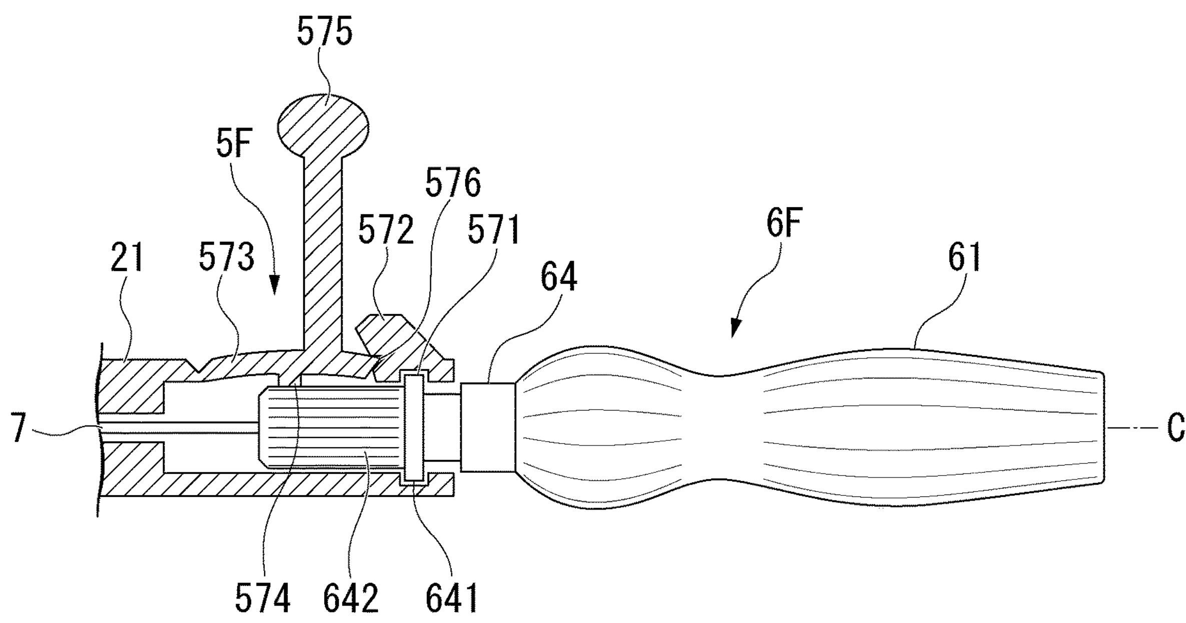
FIG. 27 is a partial cross-sectional view of the handle of the treatment tool of a modified example of the second embodiment.

The examples of the socket 5E may apply the operation portion 20 of the first embodiment. FIG. 25 to FIG. 27 show an example that the socket 5F which is the modified example of the socket 5E is attached to the operation portion 20 of the first embodiment. FIG. 25 shows an example of the second configuration. FIG. 26 shows an example of the first configuration. FIG. 27 shows a rotation manipulation state of the rotation handle in the second configuration.

As shown in FIG. 25 to FIG. 27, the rotation handle 6F includes a rim 641 and a locking portion 642 positioned at a distal side of the base portion 64. The rim 641 is formed in a ring shape and positioned at more distal side than the base portion 64. The locking portion 642 has an approximately columnar shape and is formed from a distal end of the rim 641 toward the distal side. A plurality of concave-convex portions are formed on an outer circumferential surface of the locking portion 642. The handle 61, the base portion 64, the rim 641, and the locking portion 642 are coaxially arranged.

The socket 5F is disposed on a proximal end 23F of the connection portion 21 of the handle main body 2. The socket 5F includes an insertion port 51F, a holder 571, an arm 573, a protrusion 574, and a handle 575. A distal portion of the rotation handle 6F is inserted into the insertion port 51F. The holder 571 is provided at a proximal opening portion of the insertion port 51F. The holder 571 surrounds an outer circumference of the rim 641 and holds the rim 641. The rotation handle 6F is maintained to be rotatable ant not to be advance and retract relative to the socket 5E by holding the rim 641 by the holder 571.

The arm 573 is provided such that a part of the outer circumferential wall of the socket 5F is rotatable. A distal end of the arm 595 is disposed continuously to the socket 5E, and a proximal end of the arm 595 is capable of opening and closing. A claw 576 is provided on the proximal end of the arm 595. The handle 575 is provided to protrude outward from an outer circumferential surface of the arm 595. The handle 575 is a part in which a user grasps when manipulating to open and close the arm 595. The protrusion 574 is provided integrally with the arm 573. The protrusion 574 protrudes toward an inside of the insertion port 51 F in the radial direction. A concave portion 577 is provided on a distal end surface of the holder 571. When the claw 576 is locked with the concave portion 577, the arm 573 is maintained in a closed state. When the arm 573 is closed, the protrusion 574 is locked with the locking portion 642, thereby the rotation handle becomes the second configuration.

If a user grasps the handle 575 and tilts the handle 575 toward the distal side, the arm 595 is deformed and the claw 576 is put off from the concave portion 577 and the arm 573 is opened. If the arm 573 is opened, an engagement of the protrusion 574 and the locking portion 642 is released, thereby t the rotation handle becomes the first configuration. In the first configuration, the rotation handle 6F is freely rotatable relative to the handle main body 2.

In the second configuration, the rotation handle 6F is limited to rotate by an engagement of the protrusion 574 and the locking portion 642. The rotation handle 6F does not rotate with a force smaller than the predetermined amount of force in the rotation direction. If a rotation force equal to or larger than the predetermined amount of force is applied to the rotation handle 6F, the protrusion 574 gets over a convex portion of the locking portion 642, and is capable of moving toward the concave portion adjacent to the convex portion. At this time, a click feeling is fed back to a user (user feedback, second user feedback). As shown in FIG. 27, if the arm 573 is bent, the handle 575 also move. A user can recognize the rotation handle 6F rotates with a predetermined amount by sight.

In the example shown in FIG. 23 to FIG. 27, the socket is provided at a connection part of the rotation handle with the handle main body, and the protrusion and the locking portion are provided at outside of the socket. The protrusion is supported by the arm and protrudes from an outside of the socket toward the outer circumferential surface of the socket. The first configuration releasing a lock between the protrusion with the locking portion and the second configuration locking the protrusion with the locking portion are switched due to a transition of the arm. As the result, the user can switch between the first configuration and the configuration by rotating the socket. Furthermore, since a user can visually recognize a positional relationship between the protrusion and the locking portion, a user can check by sight whether a state of the rotation handle in the first configuration or the second configuration.

In the above embodiments, the rotation handle can be used while switching between the first configuration in which the rotation handle is capable of freely rotatable and the second configuration in which a rotation of the rotation handle is limited and in which the rotation handle is capable of rotating with the predetermined amount when applied a force equal to or larger than the predetermined amount to the rotation handle.

What is claimed is:

1. A treatment tool, comprising:

a tube including a lumen extending in a longitudinal axis of the tube;

a wire inserted into the lumen and extending along the longitudinal axis of the tube;

a first handle connected to a proximal end portion of the wire; and a second handle attached to a proximal end portion of the tube;

wherein a first protrusion is provided on an outer periphery of the second handle, and a plurality of second protrusions and a plurality of recesses are provided on an inner periphery of the first handle, wherein, in a first configuration, the first protrusion is disengaged from one or more of the plurality of recesses, and wherein, in a second configuration, the first protrusion engages with one or more of the plurality of recesses.

2. The treatment tool according to claim 1, wherein the first handle includes a handle shaft and a slider slidably provided on the handle shaft, wherein the handle shaft is rotatably engaged with the second handle, wherein the slider is connected to the proximal end portion of the wire, wherein the slider is engaged with the handle shaft and is non-rotatable relative to the handle shaft and translatable to advance and retract relative to the handle shaft, wherein the treatment tool further includes an electrode provided at a distal end portion of the tube and translatable to protrude from the tube, and wherein the electrode is connected with a distal end portion of the wire.

3. The treatment tool according to claim 1, wherein the first handle is switchable between the first configuration and the second configuration by advancing and retracting the first handle relative to the second handle in a direction of a rotation axis.

4. The treatment tool according to claim 1, wherein, in the first configuration, the wire is non-twisted, and wherein, in the second configuration, the wire is twisted.

5. The treatment tool according to claim 1, wherein switching from the second configuration to the first configuration eliminates a twist of the wire.

6. The treatment tool according to claim 1, wherein in the first configuration, the first handle is rotatable relative to the second handle around a rotation axis, and wherein in the second configuration, when a force applied to the first handle in a rotational direction is equal to or less than a predetermined amount, the first handle is unrotatable relative to the second handle, and when the force applied to the first handle in a rotational direction is greater than the predetermined amount, the first handle is rotatable relative to the second handle.

7. The treatment tool according to claim 1, wherein in the second configuration, when the first handle is rotated relative to the second handle, sound is generated when the second protrusion passes over the first protrusion.

8. The treatment tool according to claim 1, wherein the second handle has a socket, which is slidably attached to the first handle, and the socket has the first protrusion.

9. The treatment tool according to claim 1, wherein the second handle has a socket, and the first configuration and the second configuration can be switched by rotating the socket.

* * * * *